(12) United States Patent
Chen et al.

(10) Patent No.: US 10,813,922 B2
(45) Date of Patent: *Oct. 27, 2020

(54) REDUCING MEMORY LOSS IN MAMMALS SUFFERING FROM ALZHEIMER'S DISEASE

(71) Applicant: The Penn State Research Foundation, University Park, PA (US)

(72) Inventors: Gong Chen, State College, PA (US); Zheng Wu, State College, PA (US); Ziyuan Guo, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/026,934

(22) Filed: Jul. 3, 2018

(65) Prior Publication Data

US 2018/0353498 A1 Dec. 13, 2018

Related U.S. Application Data

(63) Continuation of application No. 14/901,620, filed as application No. PCT/US2014/046723 on Jul. 15, 2014, now Pat. No. 10,039,756.

(60) Provisional application No. 61/906,539, filed on Nov. 20, 2013, provisional application No. 61/859,064, filed on Jul. 26, 2013.

(51) Int. Cl.
| | | |
|---|---|---|
| *A61P 25/28* | (2006.01) |
| *A61K 31/455* | (2006.01) |
| *A61K 45/06* | (2006.01) |
| *A61K 31/445* | (2006.01) |
| *A61K 31/454* | (2006.01) |
| *A61K 31/551* | (2006.01) |
| *A61K 51/04* | (2006.01) |
| *G01N 33/94* | (2006.01) |
| *A61K 9/00* | (2006.01) |
| *A61K 31/5517* | (2006.01) |
| *A61K 31/7088* | (2006.01) |
| *A61K 51/10* | (2006.01) |

(52) U.S. Cl.
CPC .......... *A61K 31/455* (2013.01); *A61K 9/0019* (2013.01); *A61K 31/445* (2013.01); *A61K 31/454* (2013.01); *A61K 31/551* (2013.01); *A61K 31/5517* (2013.01); *A61K 31/7088* (2013.01); *A61K 45/06* (2013.01); *A61K 51/0402* (2013.01); *A61K 51/0406* (2013.01); *A61K 51/1018* (2013.01); *G01N 33/9426* (2013.01); *G01N 2800/2821* (2013.01)

(58) Field of Classification Search
None
See application file for complete search history.

(56) References Cited

U.S. PATENT DOCUMENTS

2011/0092464 A1 4/2011 Barlow et al.

OTHER PUBLICATIONS

"Consensus recommendations for the postmortem diagnosis of Alzheimer's disease. The National Institute on Aging, and Reagan Institute Working Group on Diagnostic Criteria for the Neuropathological Assessment of Alzheimer's Disease," Neurobiol Aging, Jul.-Aug. 1997, 18(4 Suppl): S1-2.

(Continued)

*Primary Examiner* — Aurora M Fontainhas
(74) *Attorney, Agent, or Firm* — Fish & Richardson P.C.

(57) ABSTRACT

This document relates to methods and materials for reducing memory loss. For example, methods and materials for using inhibitors of GAT-3 polypeptide activity to reduce memory loss in mammals suffering from Alzheimer's disease are provided.

8 Claims, 13 Drawing Sheets
Specification includes a Sequence Listing.

(56) References Cited

OTHER PUBLICATIONS

Borden et al., "Cloning of the human homologue of the GABA transporter GAT-3 and identification of a novel inhibitor with selectivity for this site," Receptors Channels, 1994, 2(3): 207-13.

Brickley et al., Extrasynaptic GABAA Receptors: Their Function in the CNS and Implications for Disease. Neuron 73, Jan. 12, 2012, 23-34.

Clarkson et al., Reducing excessive GABA-mediated tonic inhibition promotes functional recovery after stroke. Nature 468, 305-309 (Nov. 11, 2010).

Faust et al., "Azetidine derivatives as novel gamma-aminobutyric acid uptake inhibitors: synthesis, biological evaluation, and structure-activity relationship," Eur J Med Chem, Jun. 2010, 45(6): 2453-66.

GenBank Accession No. CAA01920.1, GABA-A Receptor Subunits (alpha-2, alpha-3, alpha-5, alpha-6, beta-2) and transfected cells expressing them, date Apr. 14, 2005, 2 pages.

Glykys et al., "Which GBA(A) receptor subunits are necessary for tonic inhibition in the hippocampus?," J Neurosci, Feb. 2008, 28(6): 1421-6.

Hutcheon et al., "Organization of GABA receptor alpha-subunit clustering in the developing rat neocortex and hippocampus," Eur J Neurosci, May 2004, 19(9): 2475-87.

International Preliminary Report on Patentability in International Application No. PCT/US2014/046723, dated Jan. 26, 2016, 7 pages.

International Search Report and Written Opinion in International Application No. PCT/US14/46723, dated Jan. 30, 2015, 13 pages.

Jiang and Chen, "Ca2+ regulation of dynamin-independent endocytosis in cortical astrocytes," J Neurosci, Jun. 2009, 29(25): 8063-8074.

Kinney, "GAT-3 Transporters Regulate Inhibition in the Neocortex," J Neurophysiol, 2005, 94: 4533-4537.

Louzada et al., "Taurine prevents the neurotoxicity of beta-amyloid and glutamate receptor agonists: activation of GABA receptors and possible implications for Alzheimer's disease and other neurological disorders," FASEB J, Mar. 2004, 18(3): 511-8.

Mirra et al., "The Consortium to Establish a Registry for Alzheimer's Disease (CERAD). Part II. Standardization of the neuropathologic assessment of Alzheimer's disease," Neurology, Apr. 1991, 41(4): 479-86.

Montine et al., "National Insitute on Aging-Alzheimer's Association guidelines for the neuropathologic assessment of Alzheimer's disease: a practical approach," Acta Neuropathol, Jan. 2012, 123(1): 1-11.

Oakley et al., "Intraneuronal beta-amyloid aggregates, neurodegeneration, and neuron loss in transgenic mcie with five familial Alzheimer's disease mutations: potential factors in amyloid plaque formation," J Neurosci, Oct. 2006, 26(40): 10129-40.

Sperk et al., "GABA(A) receptor subunits in the rat hippocampus I: immunocytochemical distribution of 13 subunits," Neuroscience, Oct. 1997, 80(4): 987-1000.

Thomsen et al., "1-(3-(9H-carbazol-9-yl)-1-propyl)-4-(2-methoxyphenyl)-4-piperidinol, a novel subtype selective inhibitor of the mouse type II GABA-transporter," Br J Pharmacol, Mar. 1997, 120(6): 983-5.

Wu et al., "Homeostatic competition between phasic and tonic inhibition," J Biol Chem, Aug. 2013, 288(35): 25053-65.

Wu et al., "γ-Aminobutyric acid type A (GABAA) receptor a subunits play a direct rold in synaptic versus extrasynaptic targeting," J Biol Chem, Aug. 2012, 287(33): 27417-30.

Yoon et al., "The amount of astrocytic GABA positively correlates with the degree of tonic inhibition in hippocampal CA1 and cerebellum," Mol Brain, Nov. 2011, 4: 42.

FIG. 1A
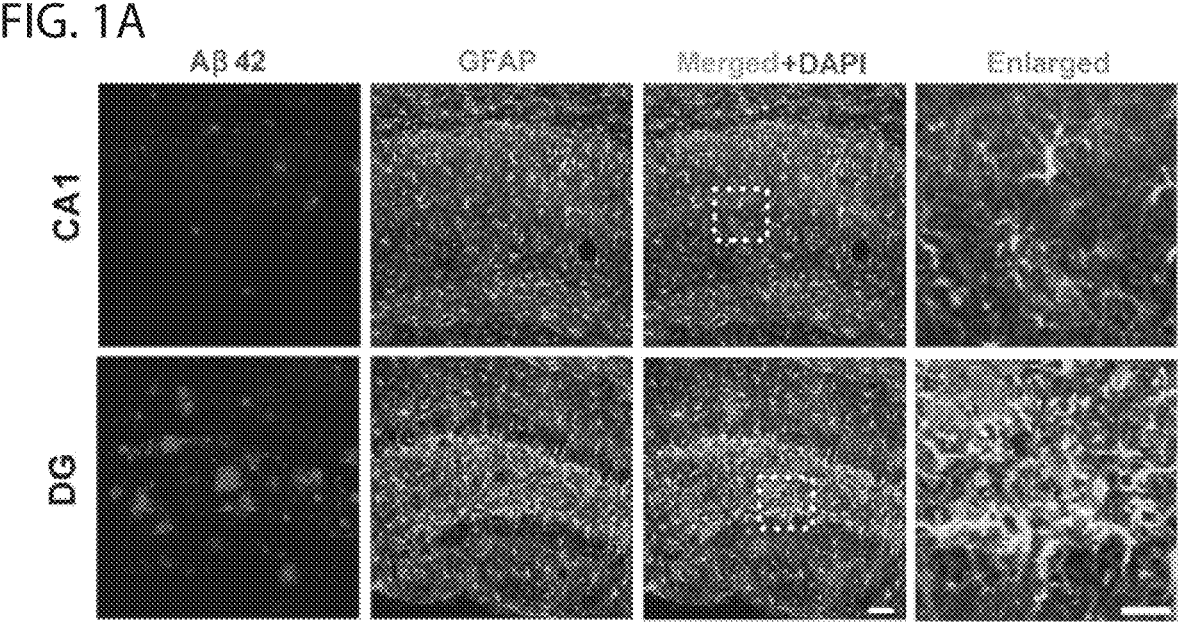
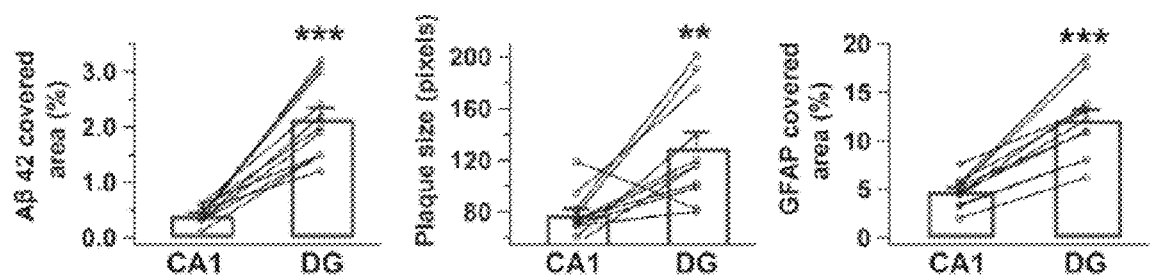
FIG. 1B

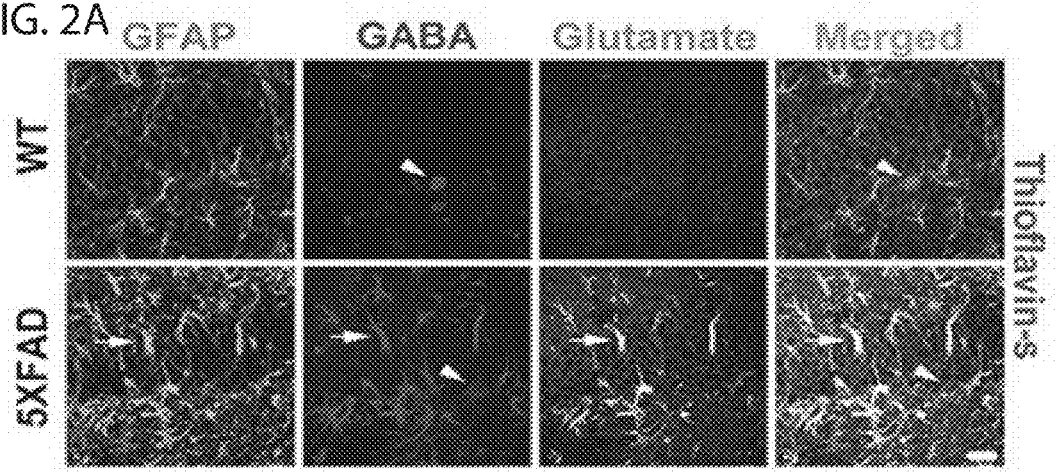
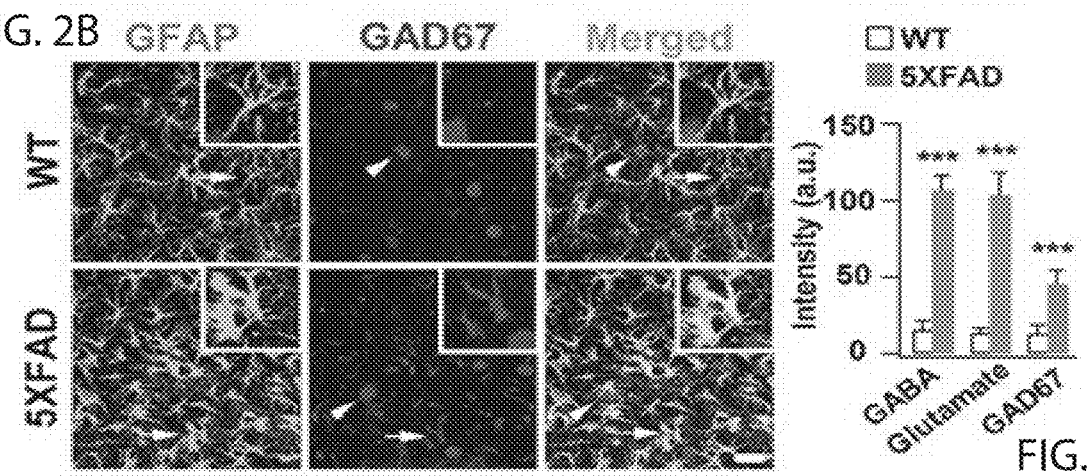
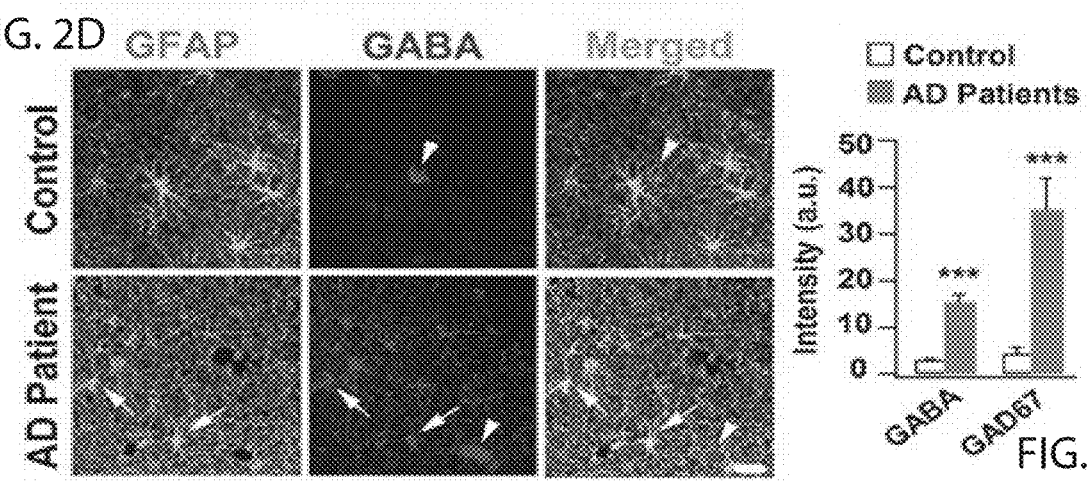

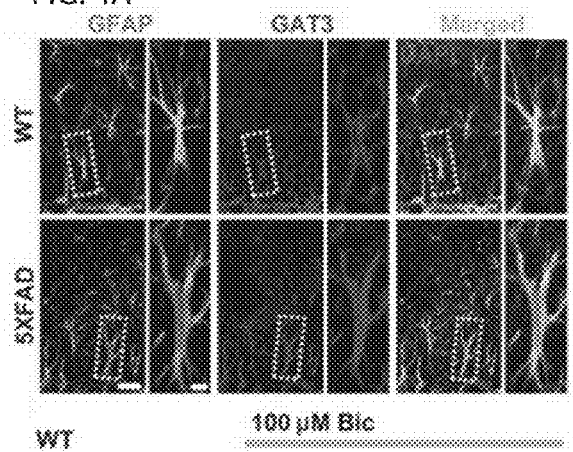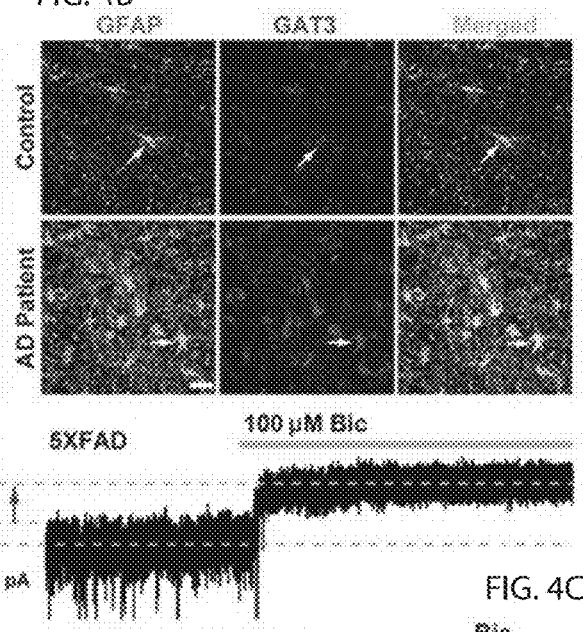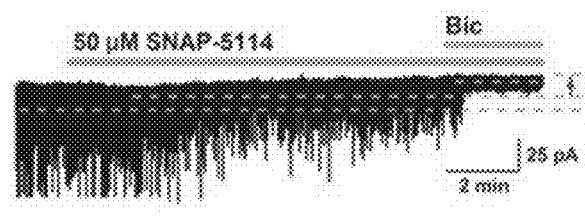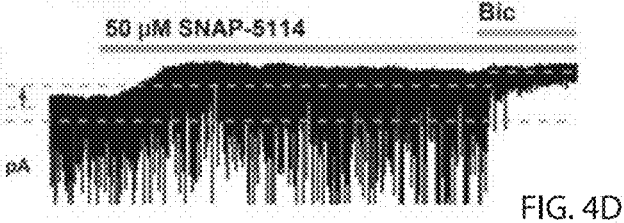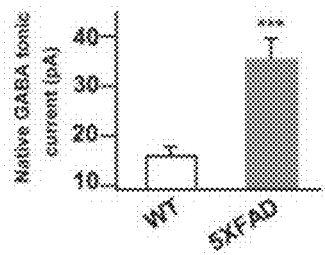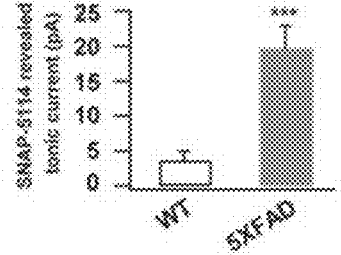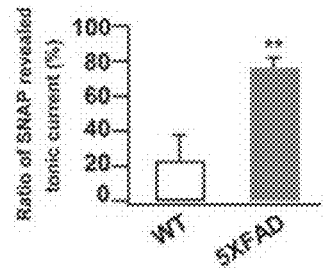

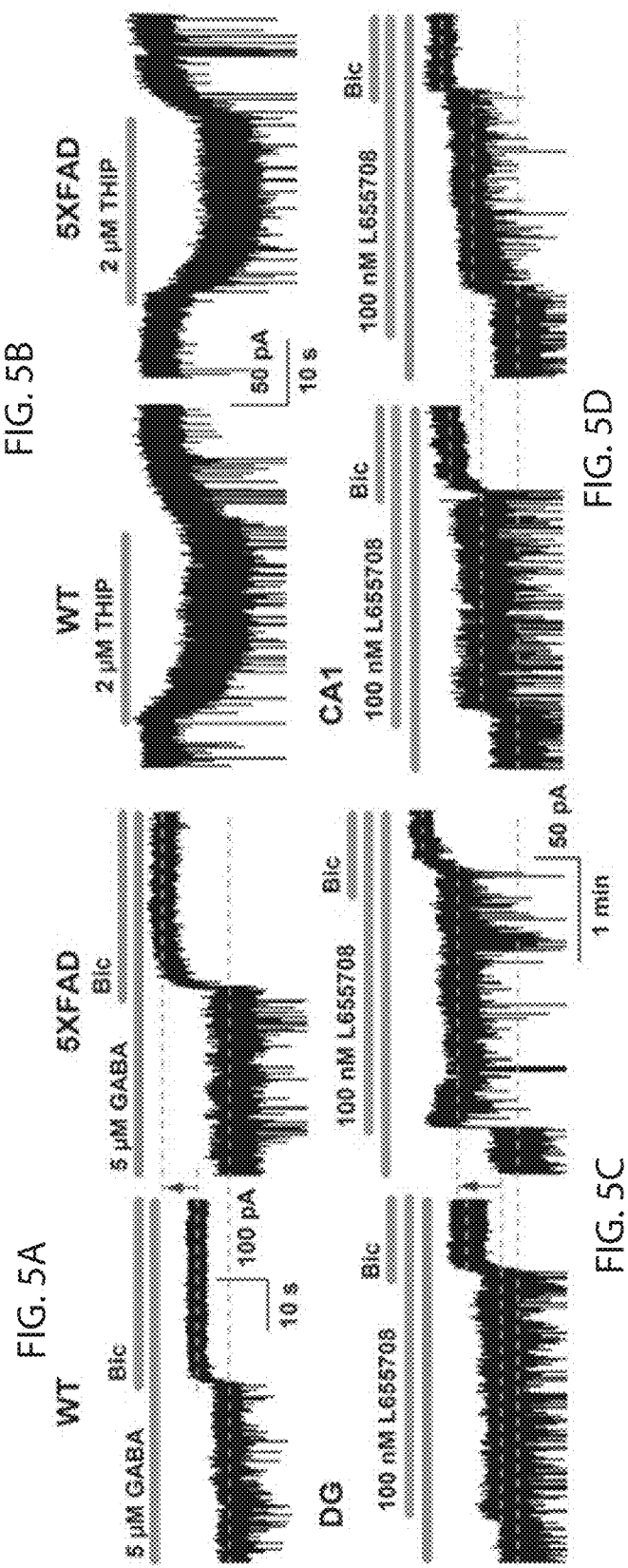

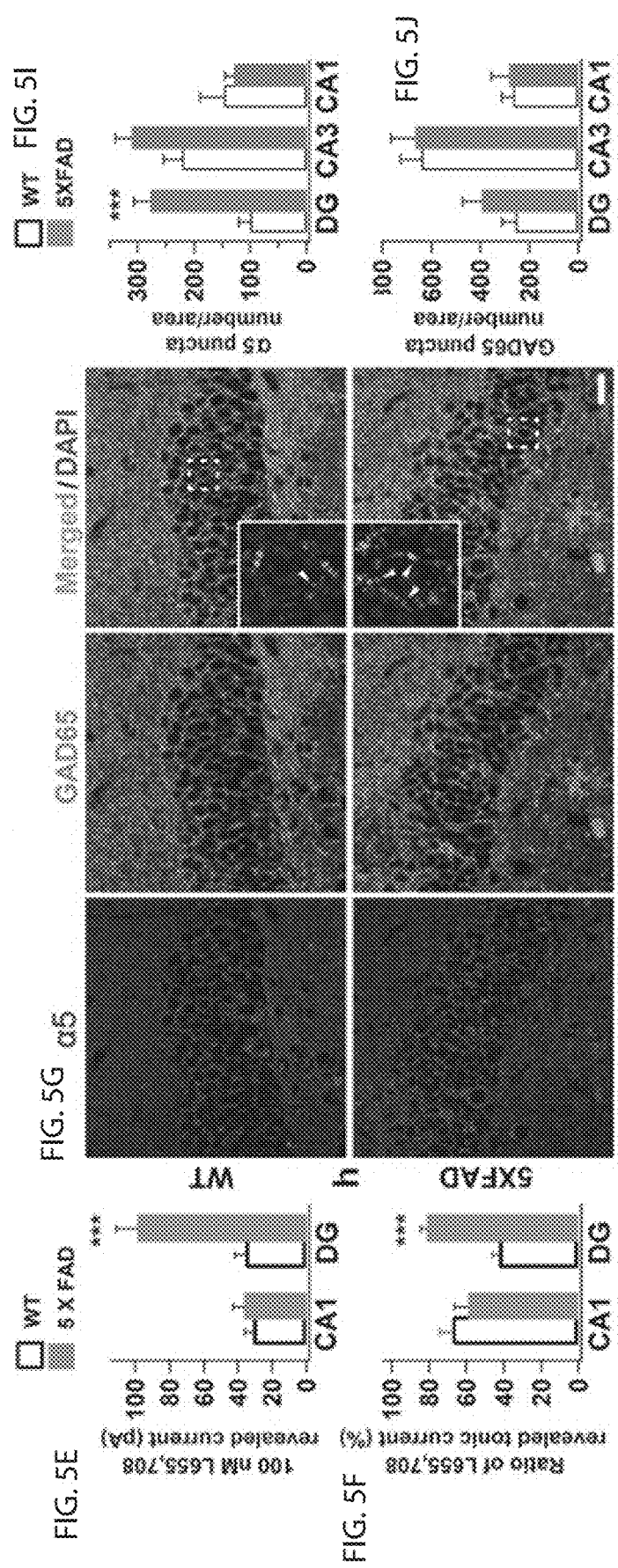

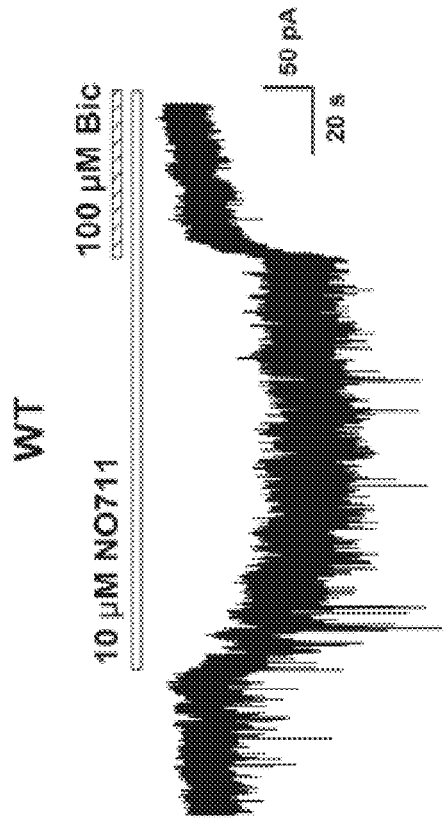
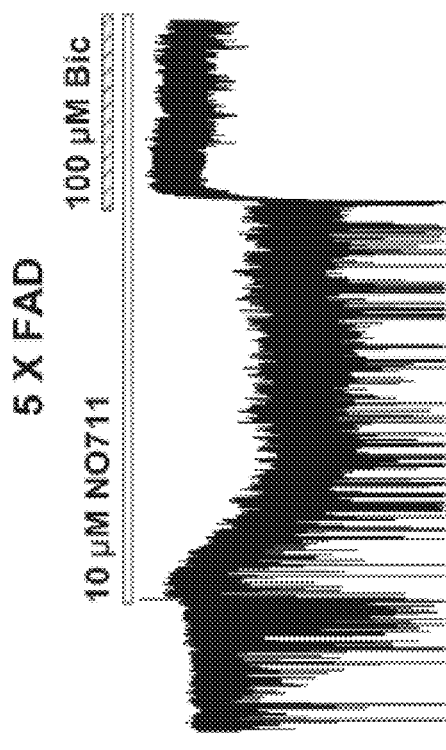
FIG. 7A
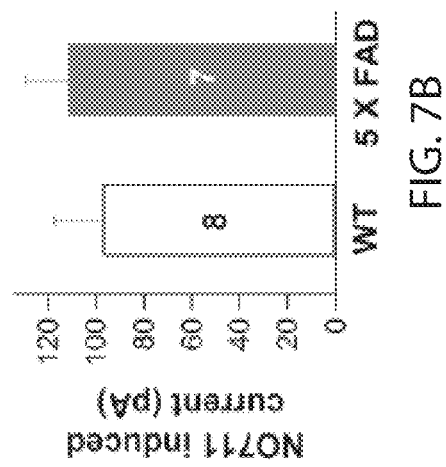
FIG. 7B

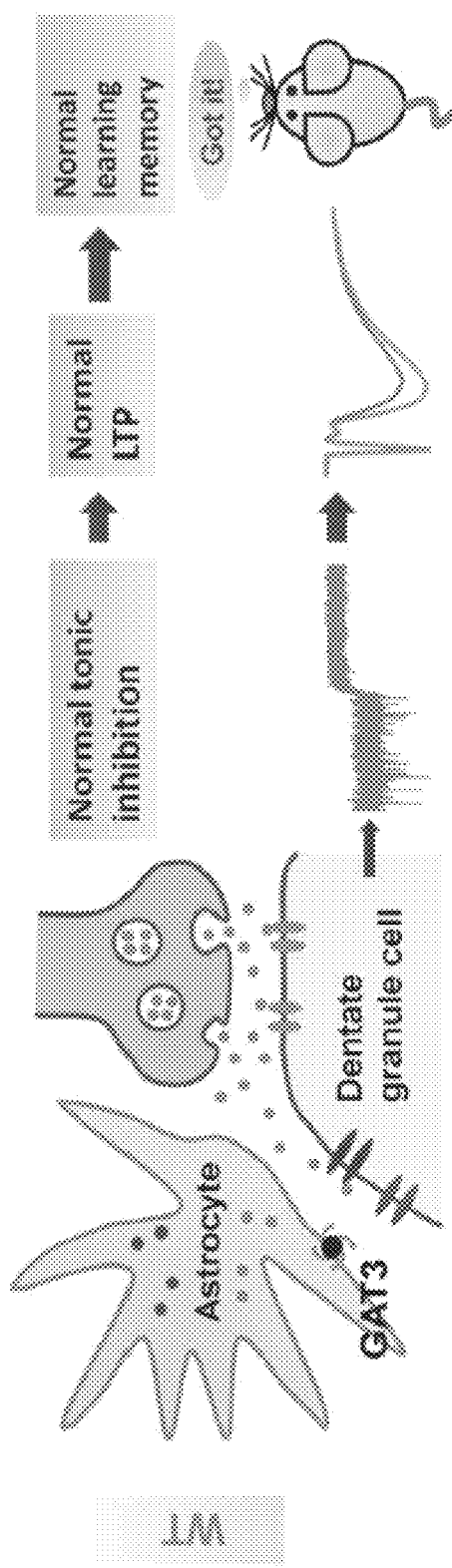
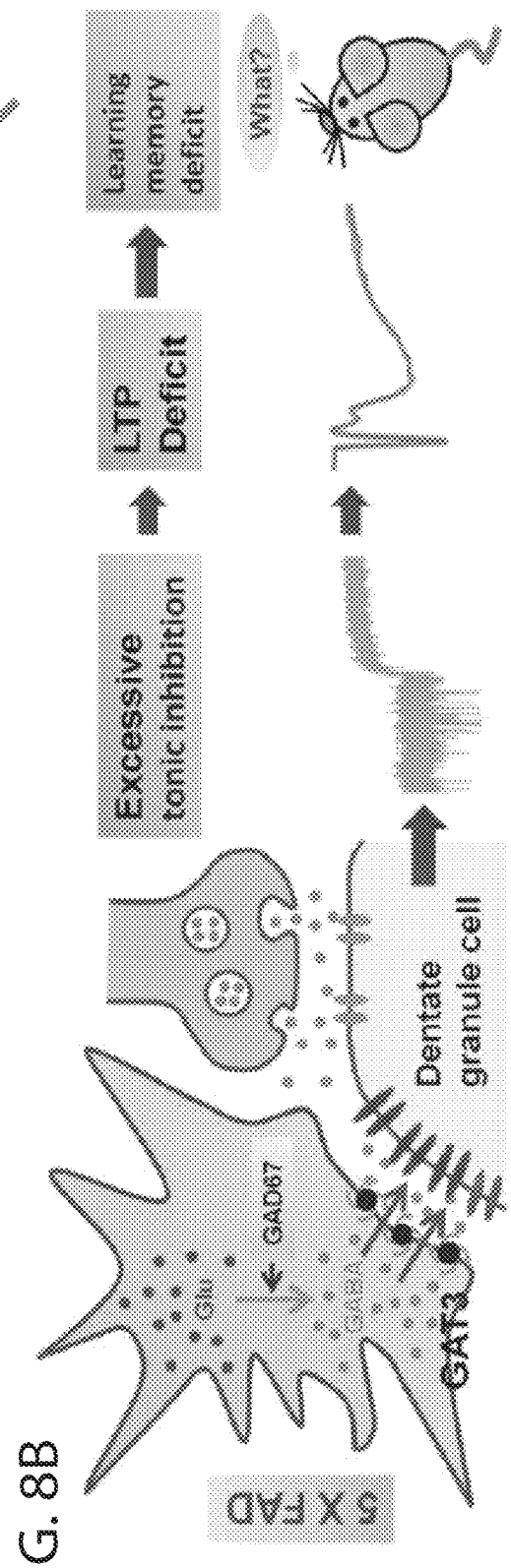
FIG. 8A
FIG. 8B

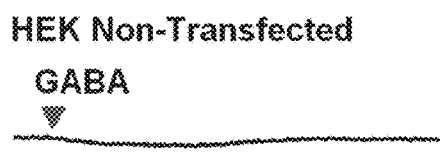
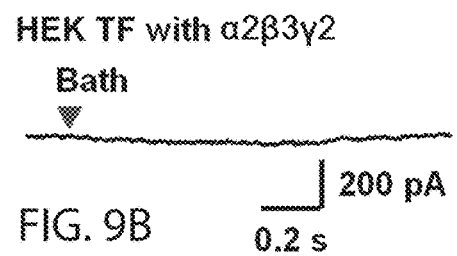
FIG. 9A
FIG. 9B
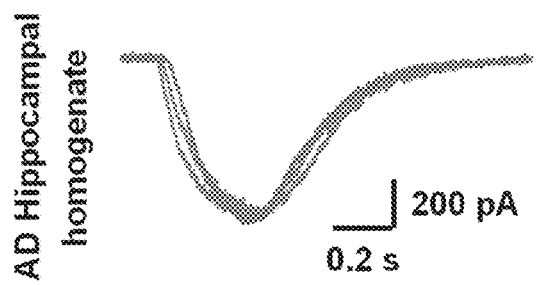
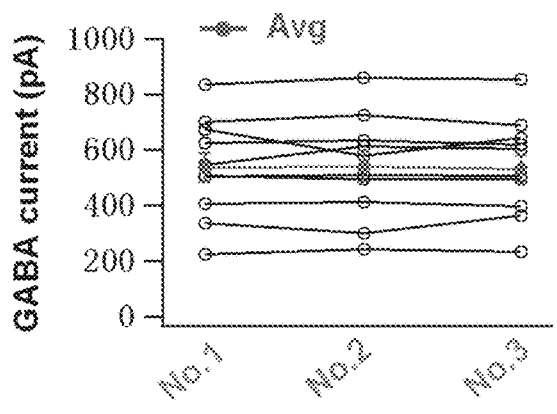
FIG. 9C
FIG. 9D
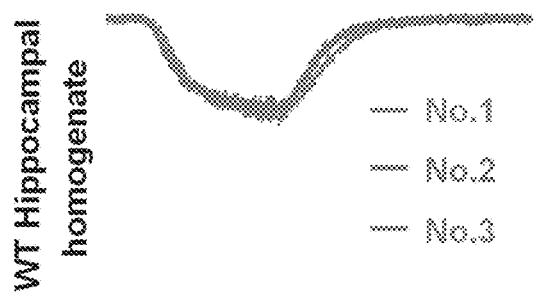
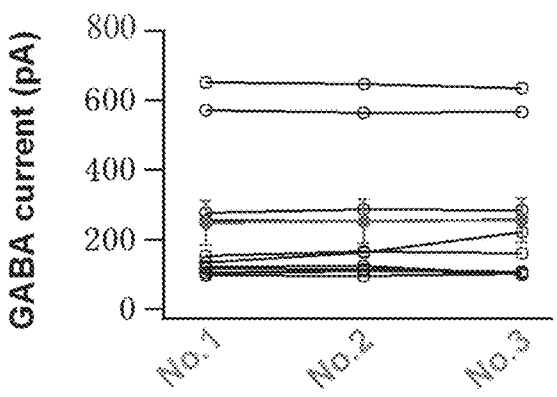
FIG. 9E
FIG. 9F

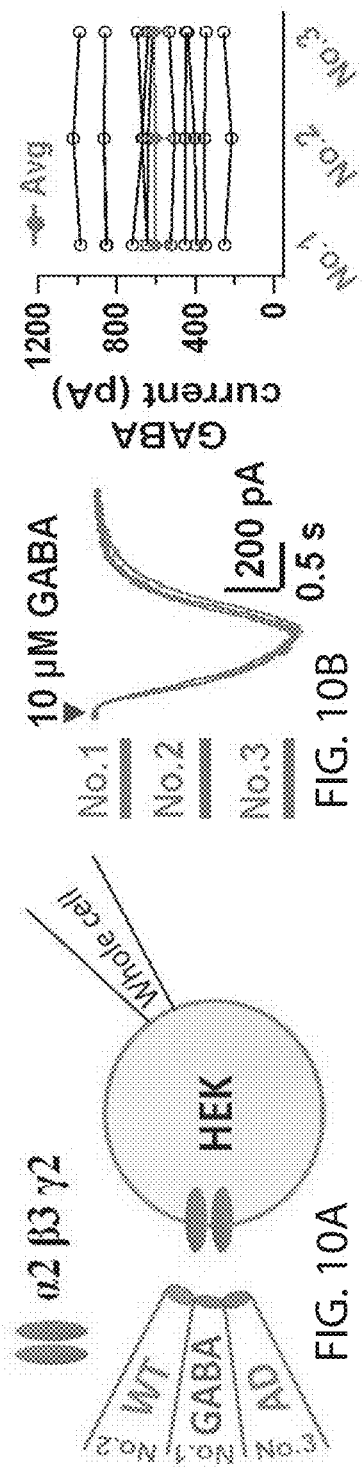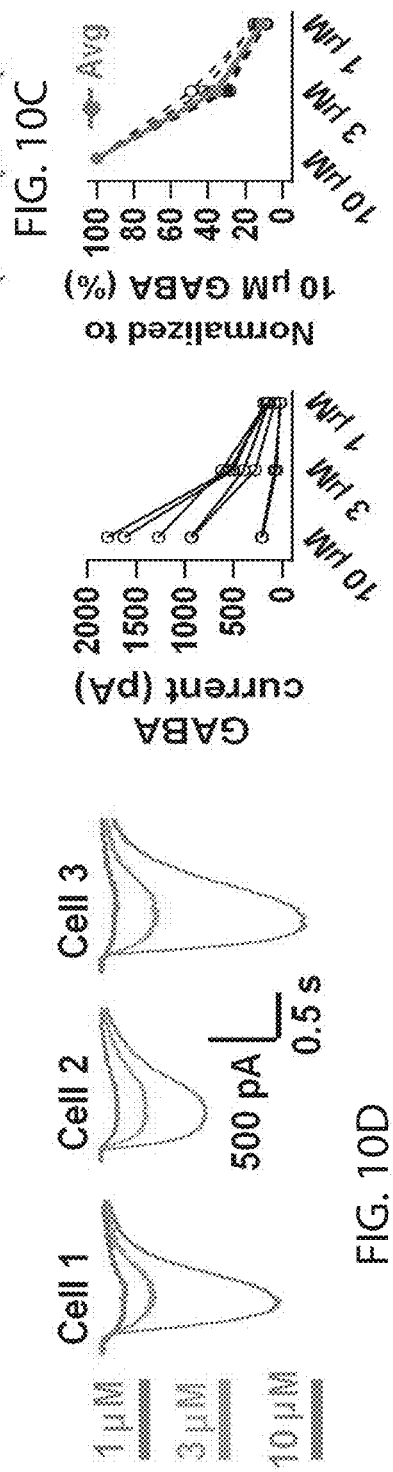

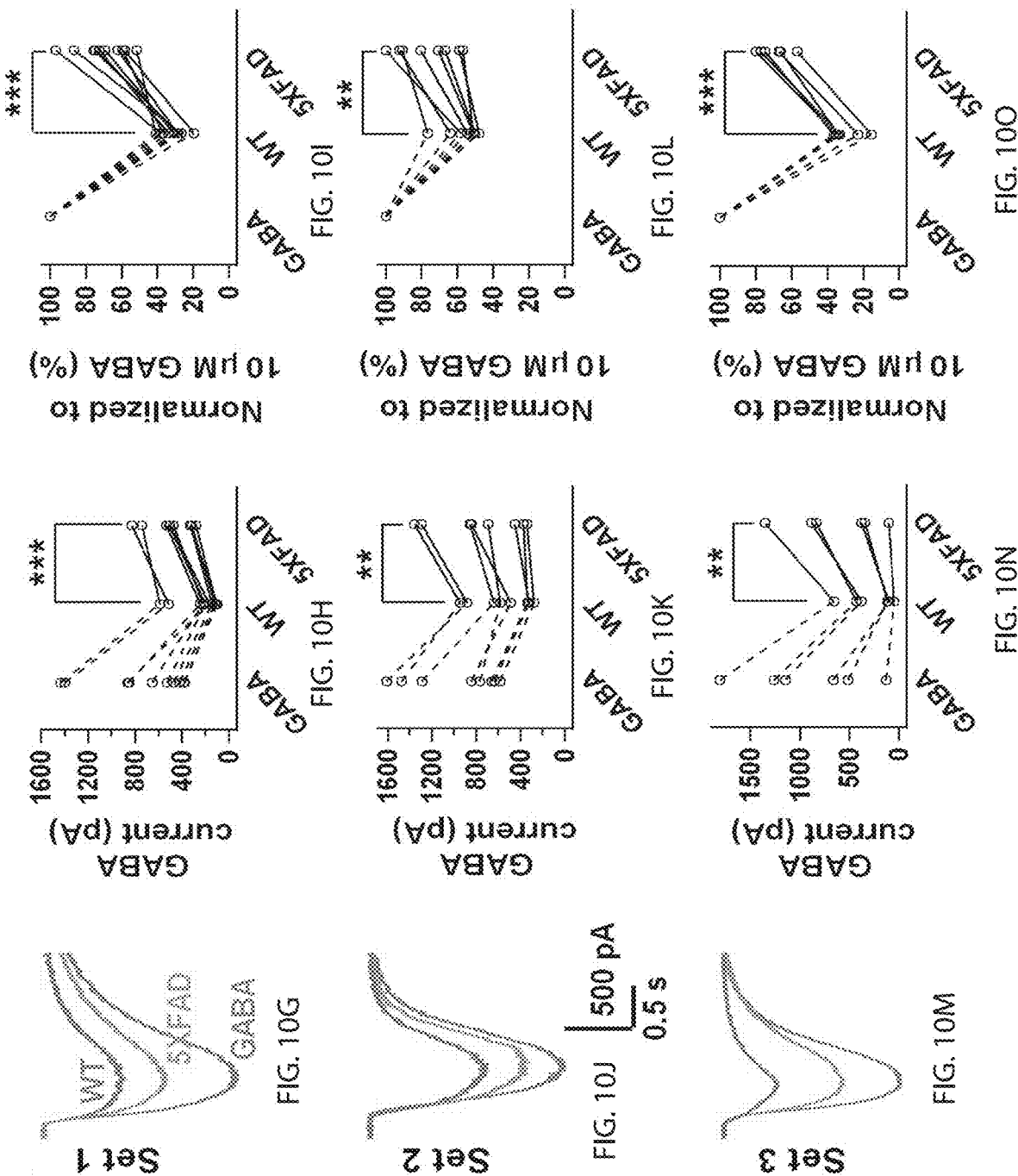

REDUCING MEMORY LOSS IN MAMMALS SUFFERING FROM ALZHEIMER'S DISEASE

CROSS-REFERENCE TO RELATED APPLICATION

This application is a continuation of U.S. application Ser. No. 14/901,620, filed Dec. 28, 2015 (now U.S. Pat. No. 10,039,756), which is a National Stage Application under 35 U.S.C. § 371 and claims the benefit of International Application No. PCT/US2014/046723, filed Jul. 15, 2014, which claims priority to U.S. Provisional Application No. 61/859,064, filed Jul. 26, 2013, and U.S. Provisional Application No. 61/906,539, filed Nov. 20, 2013. The disclosures of the foregoing applications are hereby incorporated by reference in their entirety.

STATEMENT AS TO FEDERALLY SPONSORED RESEARCH

This invention was made with government support by grants under MH083911 and MH092740 awarded by National Institutes of Health. The government has certain rights in the invention.

BACKGROUND

1. Technical Field

This document relates to methods and materials for reducing memory loss. For example, this document relates to using inhibitors of GAT-3 polypeptide activity to reduce memory loss in mammals suffering from Alzheimer's disease (AD).

2. Background Information

AD is a common form of dementia. In general, AD worsens as the disease progresses and eventually leads to death. Current treatments appear to help only with the symptoms of the disease, and there are no approved drugs that stop or reverse the progression of AD.

SUMMARY

This document provides methods and materials for reducing memory loss. For example, this document provides methods and materials for using inhibitors of GAT-3 polypeptide activity to reduce memory loss in mammals suffering from AD. As described herein, mammals suffering from AD can be administered an inhibitor of GAT-3 polypeptide activity (e.g., an inhibitor of GAT-3 polypeptide efflux of GABA from reactive astrocytes) in a manner that reduces GABA concentrations within the hippocampal dentate gyrus and that reduces memory loss. In some cases, an inhibitor of GAT-3 polypeptide activity can be used to treat AD, to reduce the progression of AD, to reduce the rate of memory loss in a mammal with AD, to improve memory in a mammal with AD, or to reverse the memory loss-induced effects in a mammal with AD.

This document also provides methods and materials for identifying a mammal as having AD. For example, detecting the presence of an elevated level of GABA in the hippocampal dentate gyrus of a mammal can indicate that that mammal has AD.

In one aspect, this document features a method for improving memory of a mammal having Alzheimer's disease. The method comprises, or consists essentially of, administering an inhibitor of GAT-3 polypeptide activity to the mammal, wherein the memory of the mammal improves following the administering. The mammal can be a human. The inhibitor can be (S)-SNAP-5114 or NNC 05-2045. The memory can improve by more than 20 percent. The memory can improve by more than 25 percent. The memory can improve by more than 30 percent. The memory can improve by more than 35 percent. The administration can comprise an intravenous administration. The method can comprise administering an inhibitor of $\alpha5$-$GABA_A$ receptor activity to the mammal. The inhibitor of $\alpha5$-$GABA_A$ receptor activity can be L-655,708. The inhibitor of $\alpha5$-$GABA_A$ receptor activity can be administered to the mammal after the inhibitor of GAT-3 polypeptide activity is administered to the mammal. The inhibitor of $\alpha5$-$GABA_A$ receptor activity can be administered to the mammal before the inhibitor of GAT-3 polypeptide activity is administered to the mammal. The inhibitor of $\alpha5$-$GABA_A$ receptor activity can be administered to the mammal as the same time as the inhibitor of GAT-3 polypeptide activity is administered to the mammal.

In another aspect, this document features a method for measuring GABA in brain tissue. The method comprises, or consists essentially of, (a) contacting a cell with a brain homogenate (e.g., a hippocampal homogenate), and (b) electrophysiologically measuring a GABA response of the cell evoked by the brain homogenate (e.g., hippocampal homogenate) to determine the concentration of GABA within the brain homogenate (e.g., hippocampal homogenate). The cell can express $\alpha2\beta3\gamma2$ GABA receptors. The cell can be a HEK293T cell. The brain homogenate (e.g., hippocampal homogenate) can be subjected to a freeze-thaw cycle. The brain homogenate (e.g., hippocampal homogenate) can be sonicated.

In another aspect, this document features a method for identifying a mammal as having AD. The method comprises, or consists essentially of, detecting the presence of an increased level of astrocytic GABA present within a mammal's brain, wherein the presence of the increased level indicates that the mammal has AD. The mammal can be a human. The increased level of astrocytic GABA can be detected following administration of radioactive GABA to the mammal. The increased level of astrocytic GABA can be detected following administration of a composition comprising anti-GABA antibodies to the mammal. The increased level of astrocytic GABA can be detected following administration of a composition comprising an astrocyte binging agent. The astrocyte binging agent can be an anti-GFAP antibody.

In another aspect, this document features a kit for use in the detection of astrocytic GABA levels. The kit comprises, or consists essentially of, (a) radioactive GABA or a GABA binding agent, and (b) an astrocyte binging agent. The kit can comprise radioactive GABA. The kit can comprise the GABA binding agent. The GABA binding agent can be an anti-GABA antibody. The astrocyte binging agent can be an anti-GFAP antibody.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and drawings, and from the claims.

DESCRIPTION OF DRAWINGS

FIGS. 1A-1B contain data demonstrating that the dentate gyrus (DG) in the hippocampus has more Aβ deposit and reactive astrocytes than CA1 region in the 5×FAD mice. FIG. 1, panel a, contains representative images showing more Aβ immunostaining (appeared in red) and reactive astrocytes (appeared in green) in DG than in CA1 region of 5×FAD mice. FIG. 1, panel b, contains quantified data showing increased Aβ-covered area, Aβ plaque size, and glial fibrillary acidic protein (GFAP)-covered area in DG compared to CA1 region in 5×FAD mice. N=11. Scale bar=50 μm, and 20 μm in enlarged images. $P<0.01$; *$P<0.001$, paired Student's t-test. Values=Mean±SEM.

FIGS. 2A-2E contain data demonstrating high GABA content in the reactive astrocytes of Alzheimer's disease brain. FIG. 2, panel a, contains photographs of triple immunostaining showing GFAP-labeled astrocytes (appeared in green) with high content of GABA (appeared in red) and glutamate (appeared in white) in the dentate gyrus (DG) of 5×FAD animals. Arrow points to astrocyte; arrowhead points to GABAergic neuron. Thioflavin-s (blue) labels Aβ plaques. FIG. 2, panel b, contains photographs showing higher expression of GAD67 (appeared in red) in the DG astrocytes (appeared in green) of 5×FAD animals. FIG. 2, panel c, contains a graph of quantified data showing significant increase of GABA, glutamate, and glutamic acid decarboxylase-67 (GAD67) in the reactive astrocytes of 5×FAD animals. GABA and glutamate staining, n=6 mice in WT and 7 mice in 5×FAD group; GAD67 staining, n=4 mice in both groups. For panels d-e, human hippocampal tissue from AD patients also showed higher GABA content (appeared in red) in the astrocytes (appeared in green). N=6 for both control and AD groups. Scale bars=20 μm. ***$P<0.001$, Student's t-test. Values=Mean±SEM.

FIGS. 4A-4G contain data demonstrating the up-regulation of astrocyte-specific GABA transporter GAT-3 and increased tonic GABA current in the dentate granule cells of 5×FAD animals. FIG. 4, panel a, contains images showing a significant increase of GAT-3 (appeared in red) in the dentate astrocytes (appeared in green) in 5×FAD animals. N=6 mice for WT or AD group. Scale bar=20 μm and 5 μm (enlarged panel). FIG. 4, panel b, contains images showing that human astrocytes (appeared in green) in AD patients also exhibited a remarkable increase of GAT-3 (appeared in red). N=6 for both control and AD groups. Scale bar=20 μm. FIG. 4, panel c, is a trace showing enhanced tonic GABA current in the dentate granule cells of 5×FAD animal revealed by GABA$_A$-R antagonist bicuculline (Bic). mIPSCs were truncated for better view of the small tonic current. FIG. 4, panel d, is a trace showing that a GAT-3 inhibitor SNAP-5114 blocked the majority of the tonic current in the 5×FAD animal. FIG. 4, panels e-g, are graphs plotting the quantified data showing an enhanced tonic current and a major contribution by GAT-3 in the dentate granule cells of 5×FAD animals. N=12 for WT, and 13 for 5×FAD group. $P<0.01$, *$P<0.001$.

FIGS. 5A-5J contain data demonstrating the up-regulation of α5-GABA$_A$ receptors in the dentate granule cells of 5×FAD animals. FIG. 5, panel a, contains traces showing enhanced tonic GABA current in the dentate granule cells of 5×FAD animals (recorded in the presence of 5 μM GABA). FIG. 5, panel b, contains traces showing no difference in THIP-induced tonic currents (mostly mediated by δ-GABA$_A$-Rs) between WT and 5×FAD animals. FIG. 5, panel c, contains traces showing that the α5-specific inverse agonist L-655,708 blocked the majority of tonic current in 5×FAD dentate granule cells. FIG. 5, panel d, contains traces showing that CA1 pyramidal neurons exhibit similar tonic currents between WT and 5×FAD animals. FIG. 5, panels e and f, contain graphs plotting quantified data showing increased tonic current mediated by the α5-GABA$_A$-Rs in DG, but not in CA1, of 5×FAD animals. FIG. 5, panels g and h, contain photographs of double immunostaining showing increased α5 puncta (appeared in red) in the dentate granule cells of 5×FAD mice. The inset shows that the majority of α5 puncta were extrasynaptic, not colocalizing with presynaptic GAD65 puncta (appeared in green). Scale bar=20 μm. FIG. 5, panels i and j, contain graphs plotting quantified data showing increased α5 puncta number, but not GAD65, in the DG of 5×FAD mice (n=6 mice for WT and 9 mice for 5×FAD group). ***$P<0.001$.

FIG. 6, panel a, is a graph plotting hippocampal slice recordings that revealed LTP impairment in the DG of 5×FAD mice (bottom trace), compared to the control animals (WT). Blocking tonic inhibition by L-655, 708 (100 nM) or SNAP-5114 (50 μM) rescued the impairment of LTP. FIG. 6, panel b, is a graph plotting quantified potentiation within 50-60 minutes after high frequency stimulation in various conditions. Two-way ANOVA revealed a significant change among genotype and drug treatments ($F (2, 56)=3.7$, $P<0.04$). Numbers in histograms indicate number of slices. FIG. 6, panel c, is a graph plotting Y-maze test results showing significant impairment of spontaneous alternation behavior in 5×FAD mice compared to WT animals. Chronic block of tonic inhibition by repeated injection of L-655,708 or SNAP-5114 for one week rescued the behavioral deficit. The numbers in the histograms indicate the number of mice. FIG. 6, panel d, is a graph plotting the total number of arm entries, which was not different among WT, 5×FAD, 5×FAD+L-655,708, and 5×FAD+SNAP-5114 groups. The numbers in the histograms indicate the number of mice. Data are presented as mean±s.e.m. * represents $P<0.05$, and ** represents $P<0.01$. These results demonstrate that blockade of astrocytic GABA transporter GAT3 or α5-GABA$_A$ receptors rescue LTP and memory deficit in 5×FAD mice.

FIGS. 7A-7B contain data demonstrating that neuronal GABA transporter is not altered in the dentate gyrus of 5×FAD mice. FIG. 7, panel a, contains typical traces showing tonic current induced by blockade of neuronal GABA transporters with NO-711 (1-[2-[[(Diphenylmethylene)imino]oxy]ethyl]-1,2,5,6-tetrahydro-3-pyridinecarboxylic acid hydrochloride hydrochloride). Large mIPSCs were truncated to better illustrate the tonic current. FIG. 7, panel b, contains quantified data showing no difference between the tonic currents revealed by NO-711 in WT vs. 5×FAD dentate granule cells ($P>0.4$).

FIGS. 8A-8B contain graphic summaries of a working model. FIG. 8, panel a, is a graphic summary where WT animals have normal levels of GABA, glutamate, and GAT-3 in astrocytes, and normal levels of δ- and α5-GABA$_A$-Rs in dentate granule cells. The tonic inhibition is small. There is significant LTP in DG, and animals have normal cognitive functions. FIG. 8, panel b, is a graphic summary where 5×FAD animals show abnormally high level of glutamate, GABA, and GAT-3 in the reactive astrocytes, and up-regulated α5-GABA$_A$-Rs in dentate granule cells. The tonic inhibition is significantly enhanced, and LTP in DG is suppressed. These animals have significant learning and memory deficits.

FIGS. 9A-9F. Control experiments for brain homogenate puff assay. (a) Puffing GABA (10 µM) onto non-transfected HEK cells did not evoke any significant responses. (b) Puffing bath solution onto GABAA-R-expressing HEK cells also not evoked any responses. (c-d) Triple micropipettes filled with the same AD hippocampal homogenate solution evoked the same size of GABA responses. (e-f) Triple micropipettes filled with the same WT hippocampal homogenate solution also evoked the same size of GABA responses, although smaller than that evoked by AD hippocampal homogenate solution.

DETAILED DESCRIPTION

Figure 3:
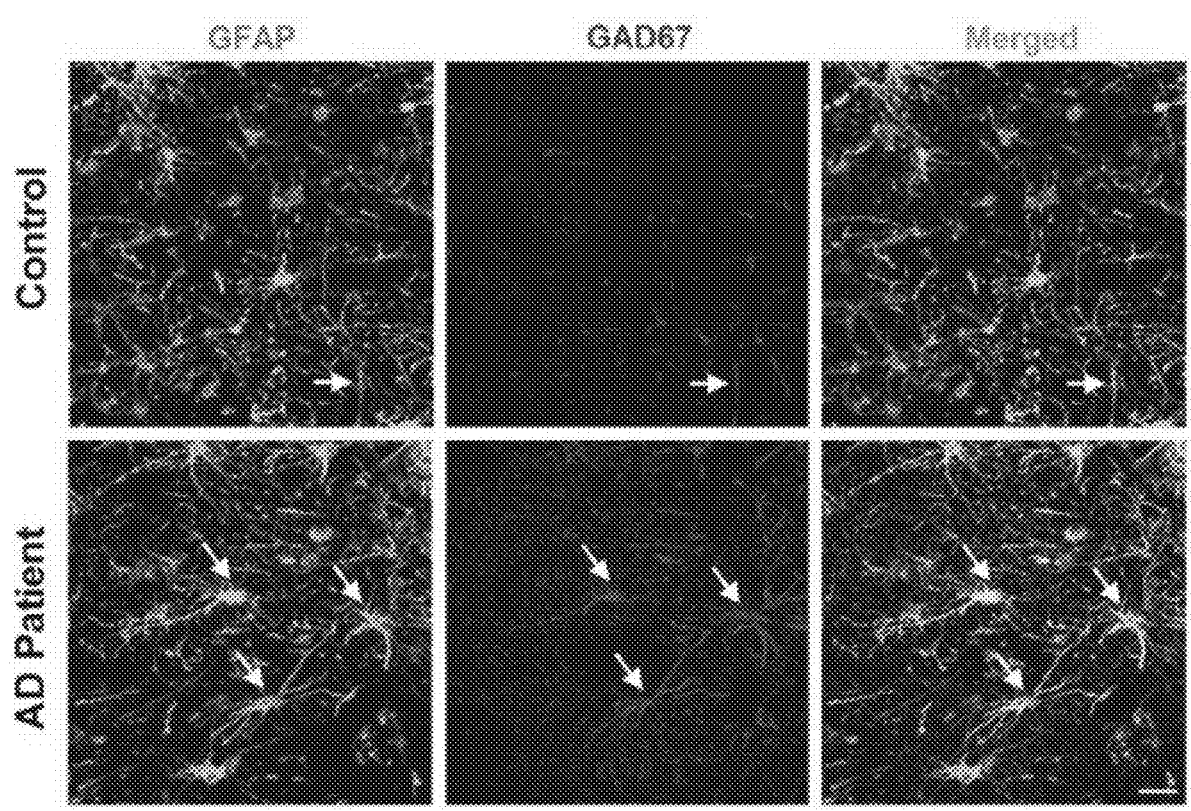
FIG. 3 contains representative images showing increased GAD67 signal (appeared in red) in human hippocampal astrocytes (appeared in green) of AD patients compared to controls. Quantified data from these images are shown in FIG. 2, panel e. Scale bar=20 μm.

This document relates to methods and materials involved in reducing memory loss. For example, this document provides methods and materials for using inhibitors of GAT-3 polypeptide activity to reduce memory loss in mammals suffering from AD. In some cases, an inhibitor of GAT-3 polypeptide activity can be used to treat AD, to reduce the progression of AD, to reduce the rate of memory loss in a mammal with AD, to improve memory in a mammal with AD, or to reverse the memory loss effects of AD in a mammal with AD. This document also provides methods and materials for identifying inhibitors of GAT-3 polypeptide activity (e.g., inhibitors of GAT-3 polypeptide efflux of GABA from reactive astrocytes).

In one embodiment, this document provides methods and materials related to treating mammals (e.g., humans) having AD. Examples of mammals that can be treated as described herein include, without limitation, humans, monkeys, dogs, cats, cows, horses, pigs, rats, and mice. A mammal can be identified as having AD using any appropriate AD diagnostic technique. For example, a physical examination, a neurological examination, a medical history review, and a mental status examination can be performed to diagnose a human as having AD. In some cases, a patient can be examined to exclude other causes of dementia that are not related to AD such as anemia, brain tumors, chronic infections, medications, severe depression, stroke, thyroid disease, and vitamin deficiencies.

As described herein, AD can be treated by administering an inhibitor of GAT-3 polypeptide activity. In some cases, an inhibitor of GAT-3 polypeptide activity can inhibit GABA efflux from reactive astrocytes and/or reduce the GABA inhibition on neighboring neurons. For example, an inhibitor of GAT-3 polypeptide activity can be administered to a human AD patient in a manner that results in reduced GABA efflux from reactive astrocytes in the dentate gyrus. In some cases, administration of an inhibitor of GAT-3 polypeptide activity to a mammal with AD can reduce the progression of AD, reduce the rate of memory loss, improve memory, or reverse the memory loss effects of AD. An example of a GAT-3 polypeptide includes, without limitation, the polypeptide having the amino acid sequence set forth in GenBank® accession number AAB33570.1 (GI No. 913242).

Examples of inhibitors of GAT-3 polypeptide activity include, without limitation, (S)-1-[2-[tris(4-methoxyphenyl) methoxy]ethyl]-3-piperidinecarboxylic acid ((S)-SNAP-5114), 1-(3-(9H-carbazol-9-yl)-1-propyl)-4-(4-methoxyphenyl)-4-piperidinol (NNC 05-2045), 1-(3-(9H-Carbazol-9-yl)-1-propyl)-4-(2-methoxyphenyl)-4-piperidino 1 (NNC 05-2090), [(−)-2-phenyl-2-[(dimethylamino)ethoxy]-(1R)-1,7,7-trimethylbi-cyclo[2.2.1]heptan] (EGYT-3886), and nipecotic acid. In some cases, an inhibitor of human GAT-3 polypeptide activity can be a selective inhibitor of human GAT-3 polypeptide activity as compared to human GAT-1 and human GAT-2 polypeptides. Examples of such selective inhibitors include, without limitation, (S)-SNAP-5114, NNC 05-2045, and NNC 05-2090. In some cases, an inhibitor of human GAT-3 polypeptide activity can be an inhibitor of human GAT-3 polypeptide activity with an IC$_{50}$ value of less than 15 µM (e.g., less than 10 less than 9 less than 8 µM, less than 7 µM, or less than 6 µM). An example of such a selective inhibitor includes, without limitation, (S)-SNAP-5114. In some cases, an inhibitor of human GAT-3 polypeptide activity that inhibits human GAT-3 polypeptide activity with an IC$_{50}$ value of less than 15 µM (e.g., less than 10 less than 9 µM, less than 8 µM, less than 7 µM, or less than 6 µM) can inhibit human GAT-1 polypeptide activity with an IC$_{50}$ value of greater than 75 µM (e.g., greater than 85 µM, greater than 90 µM, or greater than 95 µM) and can inhibit human GAT-2 polypeptide activity with an IC$_{50}$ value of greater than 15 µM (e.g., greater than 16 µM, greater than 17 µM, greater than 18 µM, or greater than 19 µM). An example of such an inhibitor includes, without limitation, (S)-SNAP-5114. In some cases, an inhibitor of human GAT-3 polypeptide activity can be an inhibitor of human GAT-3 polypeptide activity with a K$_i$ value of less than 10 µM (e.g., less than 9 µM, less than 8 µM, or less than 7 µM). An example of such an inhibitor includes, without limitation, NNC 05-2045. In some cases, an inhibitor of human GAT-3 polypeptide activity that inhibits human GAT-3 polypeptide activity with a K$_i$ value of less than 10 µM (e.g., less than 9 µM, less than 8 µM, or less than 7 µM) can inhibit human GAT-1 polypeptide activity with a K$_i$ value greater than 20 µM (e.g., greater than 22 µM, greater than 24 µM, or greater than 26 µM) and can inhibit human GAT-2 polypeptide activity with a $K_i$ value greater than 10 µM (e.g., greater than 11 µM, greater than 12 µM, or greater than 13 µM). An example of such an inhibitor includes, without limitation, NNC 05-2045.

Any appropriate method can be used to identify or confirm that a compound is an inhibitor of GAT-3 polypeptide activity or a selective inhibitor of human GAT-3 polypeptide activity. For example, the methods and materials described elsewhere (Borden et al., Receptors Channels, 2(3):207-13 (1994) and Thomsen et al., British J. Pharm., 120:983-985 (1997)) can be used to identify or confirm that a compound is an inhibitor of GAT-3 polypeptide activity or a selective inhibitor of human GAT-3 polypeptide activity.

The term "inhibit" as used herein with respect to a GAT-3 polypeptide activity refers to a greater than 15 percent reduction in GABA reuptake or GABA efflux via a GAT-3 polypeptide (e.g., a human GAT-3 polypeptide). For example, a reduction in GABA reuptake that is greater than 15 percent (e.g., greater than 20, 25, 30, 35, 40, 45, 50, 55, 60, 65, 70, 75, 80, 85, 90, 95, or 99 percent or between 15 percent and 100 percent, between 15 percent and 95 percent, between 15 percent and 90 percent, between 15 percent and 75 percent, between 15 percent and 50 percent, between 20 percent and 100 percent, between 20 percent and 95 percent, between 20 percent and 90 percent, between 20 percent and 75 percent, or between 25 percent and 75 percent) can be considered an inhibition of GABA reuptake. In some embodiments, an inhibitor of GAT-3 polypeptide activity can inhibit GABA reuptake or GABA efflux such that the reduction in GABA reuptake or GABA efflux is greater than 15 percent (e.g., greater than 15, 20, 25, 30, 35, 40, 45, 50, 55, 60, 65, 70, 75, 80, 85, 90, 95, or 99 percent) as compared to untreated controls (e.g., untreated mammals or cells). Any appropriate method can be used to assess whether or not GABA reuptake or GABA efflux has been inhibited. For example, the methods and materials described elsewhere (Borden et al., Receptors Channels, 2(3):207-13 (1994) and Thomsen et al., British J. Pharm., 120:983-985 (1997)) can be used to assess whether or not GABA reuptake or GABA efflux has been inhibited.

In some cases, one or more than one inhibitor of GAT-3 polypeptide activity can be administered to a mammal with AD to treat AD, to reduce the progression of AD, to reduce the rate of memory loss, to improve memory, or to reverse the memory loss effects of AD. For example, two, three, four, or five different inhibitors of GAT-3 polypeptide activity can be administered in combination or sequentially to a mammal with AD to treat AD, to reduce the progression of AD, to reduce the rate of memory loss, to improve memory, or to reverse the memory loss effects of AD. In one example, (S)-SNAP-5114 and NNC 05-2045 can be administered in combination or sequentially to a mammal with AD to treat AD, to reduce the progression of AD, to reduce the rate of memory loss, to improve memory, or to reverse the memory loss effects of AD.

In some cases, a nucleic acid molecule designed to induce RNA interference (e.g., an RNAi molecule or a shRNA molecule) against a GAT-3 polypeptide can be used in combination with one or more inhibitors of GAT-3 polypeptide activity or in place of an inhibitor of GAT-3 polypeptide activity. For example, an RNAi molecule designed to induce RNA interference against expression of a human GAT-3 polypeptide can be administered in combination with or sequentially with an inhibitor of GAT-3 polypeptide activity (e.g., (S)-SNAP-5114). Examples of nucleic acid molecules designed to induce RNA interference against a human GAT-3 polypeptide include, without limitation, those set forth in Table 1.

TABLE 1

Nucleic acid molecules designed to induce RNA interference against a human GAT-3 polypeptide.

| Molecule | Sequence | |
|---|---|---|
| GC1 | 5'-GCCCTTTATTTGAAGGCAT-3' | (SEQ ID NO: 1) |
| GC2 | 5'-GCATATGGAAGGGTACTAA-3' | (SEQ ID NO: 2) |
| GC3 | 5'-GCTCTTTGTGGCCATCTTT-3' | (SEQ ID NO: 3) |
| GC4 | 5'-GCACACTGCCCGAGAAATT-3' | (SEQ ID NO: 4) |
| GC5 | 5'-GCACAGGACTTATTAACAA-3' | (SEQ ID NO: 5) |
| GC6 | 5'-CCAGTGATAGTGGGCATAT-3' | (SEQ ID NO: 6) |
| GC7 | 5'-CCACCTCACCAAGATAATT-3' | (SEQ ID NO: 7) |
| GC8 | 5'-GCCTCTGATGTTCAGTCAT-3' | (SEQ ID NO: 8) |
| GC9 | 5'-CCTCTGATGTTCAGTCATT-3' | (SEQ ID NO: 9) |

Nucleic acid molecules designed to induce RNA interference against GAT-3 polypeptide expression can be administered to a mammal using any appropriate method. For example, a nucleic acid designed to induce RNA interference against GAT-3 polypeptide expression can be administered to a mammal using a vector such as a viral vector.

In some cases, an anti-GAT-3 antibody having the ability to inhibit GAT-3 polypeptide activity (e.g., GAT-3 polypeptide efflux of GABA from reactive astrocytes) can be used as an inhibitor of GAT-3 polypeptide activity as described herein. For example, anti-GAT-3 antibody having the ability to inhibit GAT-3 polypeptide activity can be administered in combination with or sequentially with (S)-SNAP-5114.

In some cases, an inhibitor of α5-GABA$_A$ receptor activity can be used in combination with one or more inhibitors of GAT-3 polypeptide activity or in place of an inhibitor of GAT-3 polypeptide activity. For example, an inhibitor of α5-GABA$_A$ receptor activity can be administered in combination with or sequentially with an inhibitor of GAT-3 polypeptide activity (e.g., (S)-SNAP-5114) to treat AD, to reduce the progression of AD, to reduce the rate of memory loss, to improve memory, or to reverse the memory loss effects of AD as described herein. Examples of inhibitors of α5-GABA$_A$ receptor activity include, without limitation, 11,12,13,13a-tetrahydro-7-methoxy-9-oxo-9H-imidazo[1,5-a]pyrrolo[2,1-c][1,4]benzodiazepine-1-carboxylic acid, ethyl ester (L-655,708); 3-bromo-10-(difluoromethyl)-9H-benzo[f]imidazo[1,5-a][1,2,4]triazolo[1,5-d][1,4]diazepine (Ro4938581, and a related derivative RG-1662); 3-(5-methylisoxazol-3-yl)-6-[(1-methyl-1H-1,2,3-triazol-4-yl) methoxy] [1,2,4]triazolo[3,4-a]phthalazine (α5IA); 1,2-diazine (also known as orthodiazine, oizine, and pyridazine); 6,6-dimethyl-3-(2-hydroxyethyl)thio-1-(thiazol-2-yl)-6,7-dihydro-2-benzothiophene-4(5H)-one (TB-21007); and 8-chloro-3-(methoxymethyl)-5-methyl-4H-imidazo[1,5-a] [1,4]benzodiazepin-6-one (PWZ-029). An example of an α5-GABA$_A$ receptor polypeptide includes, without limitation, the polypeptide having the amino acid sequence set forth in GenBank® accession number CAA01920 (GI No. 1247500).

In some cases, a combination of compounds provided herein can be administered to a mammal. For example, two, three, four, or five compounds can be administered together to a mammal to treat AD, to reduce the progression of AD, to reduce the rate of memory loss, to improve memory, or to reverse the memory loss effects of AD as described herein. In some cases, one or more compounds that can inhibit GAT-3 polypeptide efflux of GABA and one or more compounds that can inhibit α5-GABA$_A$ receptor activity can be administered together to a mammal having AD to treat AD, to reduce the progression of AD, to reduce the rate of memory loss, to improve memory, or to reverse the memory loss effects of AD as described herein.

In some cases, an inhibitor of GAT-3 polypeptide activity provided herein or an inhibitor of α5-GABA$_A$ receptor activity provided herein can be chemically converted from its free base form to a pharmaceutically acceptable salt by reacting the free base with an equivalent amount of an acid that forms a non-toxic salt. Such acids can be either inorganic or organic including, without limitation, hydrochloric acid, hydrobromic acid, fumaric acid, maleic acid, succinic acid, sulfuric acid, phosphoric acid, tartaric acid, acetic acid, citric acid, and oxalic acid. In some cases, an inhibitor of GAT-3 polypeptide activity or a pharmaceutically acceptable salt thereof provided herein can be administered to a mammal by itself or in combination with a carrier. Such carriers include, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. In some cases, preservatives, flavorings, and other additives such as, for example, antimicrobials, anti-oxidants, chelating agents, inert gases, and the like can be present. It will be appreciated that an inhibitor of GAT-3 polypeptide activity or a pharmaceutically acceptable salt thereof provided herein that is to be administered to a mammal can contain zero, one, or more than one commonly known pharmaceutically acceptable carriers.

An effective amount of a compound provided herein (e.g., an inhibitor of GAT-3 polypeptide activity such as an anti-GAT-3 antibody, a selective inhibitor of GAT-3 polypeptide activity, or a nucleic acid molecule designed to induce RNA interference against GAT-3 polypeptide expression) can be administered to a mammal having AD to treat AD, to reduce the progression of AD, to reduce the rate of memory loss, to improve memory, or to reverse the memory loss effects of AD as described herein. The term "effective" as used herein refers to any amount that induces a desired level of GAT-3 polypeptide activity inhibition while not inducing significant toxicity in the mammal. Such an amount can be determined using the methods and materials provided herein. Some compounds may have a relatively broad concentration range that is effective while others may have a relatively narrow effective concentration range. In addition, the effective amount can vary depending upon the specific mammal or the specific state of the AD to be treated because certain mammals and stages of AD can be more or less responsive to a particular compound. Such effective amounts can be determined for individual compounds using commonly available or easily ascertainable information involving equilibrium dissociation constants, mammal toxicity concentrations, and bioavailability. For example, non-toxic compounds typically can be directly or indirectly administered to a mammal in any amount that induces a desired level of GAT-3 polypeptide activity inhibition in that mammal.

Using the information provided herein, such effective amounts also can be determined by experimentation in vitro or in vivo. For example, a patient having AD can receive direct administration of a compound provided herein in an amount to achieve a blood level close to the equilibrium dissociation constant (i.e., $K_d$) calculated from in vitro analysis sufficient to inhibit GAT-3 polypeptide GABA efflux. If the patient fails to respond, then the amount can be increased by, for example, two fold. After receiving this higher concentration, the patient can be monitored for both responsiveness to the treatment and toxicity symptoms, as well as blood levels of the drug, and adjustments made accordingly.

Various factors can influence the actual effective amount used for a particular application. For example, the frequency of administration, duration of treatment, rate of metabolism of the drug, combination of other compounds, and site of administration may require an increase or decrease in the actual effective amount administered.

The frequency of administration can be any frequency that induces a desired level of GAT-3 polypeptide activity inhibition within a mammal without producing significant toxicity to the mammal. For example, the frequency of administration can be from about twice a day to about once a month, or more specifically, from about once a day to about once a week. In addition, the frequency of administration can remain constant or can be variable during the duration of treatment. As with the effective amount, various factors can influence the actual frequency of administration used for a particular application. For example, the effective amount, duration of treatment, rate of metabolism of the drug, combination of other compounds, and site of administration may require an increase or decrease in administration frequency.

An effective duration for administration of a compound provided herein can be any duration that induces a desired level of GAT-3 polypeptide activity inhibition within a mammal without producing significant toxicity to the mammal. Thus, the effective duration can vary from several days to several weeks, months, or years. In general, the effective duration for the treatment of AD can range in duration from several months to several years. Once the compound administrations are stopped, however, memory loss from AD may progress further. Thus, the effective duration can last in some cases for as long as the individual is alive.

Multiple factors can influence the actual effective duration used for a particular treatment regimen. For example, an effective duration can vary with the frequency of compound administration, effective compound amount, combination of multiple compounds, and site of administration. It is noted that diagnostic algorithm methods can be devised to determine or reflect appropriate effective doses, durations, and frequencies.

The level of toxicity, if any, can be determined by assessing a mammal's clinical signs and symptoms before and after administering a known amount of a particular composition. It is noted that the effective amount of a particular composition administered to a mammal can be adjusted according to a desired outcome as well as the mammal's response and level of toxicity. Significant toxicity can vary for each particular mammal and each particular composition.

Any combination of compounds provided herein can be administered to a mammal. For example, two compounds can be administered together to a mammal to inhibit GAT-3 polypeptide efflux of GABA in that mammal. In another example, one or more compounds that can inhibit GAT-3 polypeptide efflux of GABA and one or more compounds that can inhibit α5-GABA$_A$ receptor activity can be administered together to a mammal having AD to treat AD, to reduce the progression of AD, to reduce the rate of memory loss, to improve memory, or to reverse the memory loss effects of AD as described herein. The efficacy of such combinations can be assessed using the methods and materials provided herein.

A compound or combination of compounds provided herein can be administered to any part of a mammal's body. For example, a compound or combination of compounds provided herein can be delivered the brain (e.g., the dentate gyrus) of a mammal. In some cases, a compound or combination of compounds provided herein can be administered intravenously, intraperitoneally, intramuscularly, subcutaneously, intrathecally, intracerebroventricularly, intradermally, orally, by inhalation, or by gradual perfusion over time.

In some cases, the methods and materials provided herein can be used to treat dementia or improve memory in a mammal suffering from dementia not associated with AD. For example, an inhibitor of GAT-3 polypeptide activity can be administered as described herein to a mammal having dementia, but not AD, in a manner that results in improved memory.

This document also provides methods and materials for identifying a mammal as having AD. For example, detecting the presence of an elevated level of GABA in the hippocampal dentate gyrus of a mammal can indicate that that mammal has AD. Any appropriate method can be used to determine the level of GABA present within the hippocampal dentate gyrus region of a mammal. For example, microdialysis, HPLC, and mass spectrometry techniques can be used to measure GABA levels within the hippocampal dentate gyrus region of a mammal or in a tissue sample (e.g., a small tissue sample) removed surgically from a patient.

The term "elevated" as used herein with respect to the level of GABA within the hippocampal dentate gyrus region of a mammal (e.g., a human) is any level that is at least about 10 percent greater than a reference level for GABA within the hippocampal dentate gyrus region of a mammal. The term "reference level" as used herein with respect to GABA within the hippocampal dentate gyrus region of a mammal is the level of GABA typically present within the hippocampal dentate gyrus region of normal mammals free of dementia or free of AD. For example, a reference level of GABA within the hippocampal dentate gyrus region of a mammal can be the average level of GABA within the hippocampal dentate gyrus region of a random sampling of 50 humans free of AD. It will be appreciated that levels from comparable samples and comparable mammals are used when determining whether or not a particular GABA level is an elevated level. For example, the average level of GABA present within the hippocampal dentate gyrus region from a random sampling of healthy mice may be X units/g of tissue, while the average level of GABA present within the hippocampal dentate gyrus region from a random sampling of healthy humans may be Y units/g of tissue. In this case, the reference level for GABA in mouse tissue would be X units/g of tissue, and the reference level for GABA in human tissue would be Y units/g of tissue. Thus, when determining whether or not the level of GABA in human tissue is elevated, the measured level would be compared to the reference level for GABA present in human tissue. In some cases, the reference level of GABA can be a ratio of a value of GABA in a sample to a value of a control molecule in the sample. A control molecule can be any molecule that has a minimal variation in concentration across various samples of the type for which the molecule serves as a control. For example, actin, tubulin, or GAPDH can be used as control molecule when assessing GABA levels.

An elevated level of GABA within the hippocampal dentate gyrus region can be any level provided that the level is at least about 10 percent greater than a corresponding reference level for GABA. For example, an elevated level of GABA can be at least about 10, 15, 20, 30, 40, 50, 60, 70, 80, 90, 100, or more percent greater than the reference level for GABA.

In some cases, detecting the presence of an increased level of GABA from reactive astrocytes within the brain (e.g., the hippocampal dentate gyrus) of a mammal can indicate that that mammal has AD. Any appropriate method can be used to determine the level of GABA present from reactive astrocytes of a mammal. For example, radioactive GABA can be administered to a mammal to label the astrocytic GABA present within the mammal's brain, and an X-ray detection device can be used to detect the location and amount of radioactive GABA. An increased level of radioactive GABA (e.g., a 10, 15, 20, 30, 40, 50, 60, 70, 80, 90, 100, or more percent increase) within regions containing astrocytes (e.g., the hippocampal dentate gyrus) as compared to the levels observed in control mammals known to lack AD can indicate that the mammal has AD. In another example, particles (e.g., micro- or nano-particles) conjugated with an anti-GABA antibody or other GABA-binding agent can be administered to a mammal to label the astrocytic GABA present within the mammal's brain. These particles can be designed to emit fluorescence or display a different electron dense property so that they can be detected by MRI or PET scanning or multi-photon imaging techniques. Thus, after the particles are administered to a mammal (e.g., a human) to be tested, MRI or PET scanning or multi-photon imaging techniques can be performed to determine the levels of GABA within different brain regions. An increased level of radioactive GABA (e.g., a 10, 15, 20, 30, 40, 50, 60, 70, 80, 90, 100, or more percent increase) within regions containing astrocytes (e.g., the hippocampal dentate gyrus) as compared to the levels observed in control mammals known to lack AD can indicate that the mammal has AD. In some cases, anti-GFAP antibodies, anti-S100-beta antibodies, anti-GM antibodies, and/or anti-Aldh111 antibodies can be used to label astrocytes to aid in the co-localization of astrocytes and GABA. For example, particles (e.g., micro- or nano-particles) conjugated with an anti-GABA antibody can be co-administered to a mammal with particles (e.g., micro- or nano-particles) conjugated with an anti-GFAP antibody. In these cases, MRI or PET scanning or multi-photon imaging techniques can be performed to determine the levels of GABA and the location of astrocytes within different brain regions.

This document also provides kits for detecting AD in a mammal (e.g., a human). For example, a kit can be designed to include a molecule capable of detecting GABA levels within a mammal or the location of GABA within a mammal in combination with a molecule capable of detecting astrocytes within a mammal. Examples of molecules capable of detecting GABA levels or the location of GABA within a mammal include, without limitation, labeled GABA (e.g., radioactive GABA or fluorescently-labeled GABA) and GABA binding agents. Examples of GABA binding agents include, without limitation, anti-GABA antibodies, GABA receptors (e.g., purified GABA receptors), and GABA transporters. Examples of molecules capable of detecting astrocytes within a mammal include, without limitation, astrocyte binding agents such as anti-GFAP antibodies, anti-S100-beta antibodies, anti-GM antibodies, and anti-Aldh111 antibodies. In some cases, a GABA binding agent, an astrocyte binding agent, or both can be conjugated to a particle to aid in detection. For example, a GABA binding agent can be conjugated to a micro- or nano-particle to form a micro- or nano-particle containing a GABA binding agent, and an astrocyte binding agent can be conjugated to a micro- or nano-particle to form a micro- or nano-particle containing an astrocyte binding agent. In these cases, the particles containing a GABA binding agent can be administered separately or together with the particles containing an astrocyte binding agent.

Once the reagents of the kit are administered to a mammal to be tested, appropriate detection methods (e.g., X-ray detection, MRI, or PET scanning or multi-photon imaging techniques) can be performed to assess the levels and locations of GABA within the mammal's brain. If an increased level of astrocytic GABA is determined to be present, then that mammal can be classified as having AD.

The invention will be further described in the following examples, which do not limit the scope of the invention described in the claims.

EXAMPLES

Example 1—Excessive GABA Release from Reactive Astrocytes and Up-Regulated α5-GABA$_A$ Receptors Enhance Tonic Inhibition in the Dentate Gyrus of Alzheimer's Brain Experimental Animals 5×FAD transgenic mice were purchased from the Jackson Lab (stock number: 006554), carrying mutations on both human APP (Swedish (K670N/M671L), Florida (I716V), and London (V7170) and human PS1 proteins (M146L and L286V) (Oakley et al., *J. Neurosci.*, 26(40):10129-10140 (2006)). This transgenic line was crossed with the C57BL/6 mice for breeding. Both male and female mice at 6-8 months old (5×FAD and age-matched WT littermates) were used. Mice were housed in a 12 hour light/dark cycle and supplied with enough food and water.

Human Case Material

Hippocampal tissue was provided by the Emory University Alzheimer's Disease Center and Center for Neurodegenerative Disease Brain Bank from 6 cases meeting CERAD (Mirra et al., *Neurology* 41(4):479-486 (1991)), NIA-Reagan (*Neurobiol Aging*, 18(4 Suppl):S1-2 (1997)), and National Institute on Aging-Alzheimer's Association (Montine et al., *Acta Neuropathol.*, 123(1):1-11 (2012)) criteria for the neuropathologic diagnosis of Alzheimer's disease (see Table 2 for case information). Tissues from six controls with no history of neurological disease and no significant neuropathologic changes also were provided.

TABLE 2

Summary information for human hippocampal tissue.

| Case number | PMI (hr) | Age at onset | Age at death | Race/Sex |
|---|---|---|---|---|
| AD PATIENTS | | | | |
| OS03-163 | 4.5 | <52 | 55 | W/F |
| E04-76 | 30.5 | 65 | 72 | W/M |
| E05-04 | 4.5 | 52 | 64 | W/F |
| E05-145 | 13 | 74 | 87 | W/F |
| E06-155 | 6.5 | 56 | 67 | W/M |
| E07-38 | 12 | 70 | 77 | W/M |
| CONTROL CASES | | | | |
| OS01-127 | 22.5 | | 34 | W/F |
| OS02-35 | 6 | | 75 | W/F |
| OS03-390 | 7 | | 74 | W/F |
| E05-74 | 6 | | 59 | B/M |
| E06-113 | 4.5 | | 20 | B/F |
| E06-114 | 6.5 | | 53 | B/M |

Immunohistochemistry

For mouse brain tissue immunostaining, mice were deeply anesthetized with 2.5% Avertin and then perfused with saline solution (0.9% NaCl) to wash off blood in the brain, followed by perfusing ice cold 4% paraformaldehyde (PFA) to fix the brain. Brain was dissected out and post fixed overnight in 4% PFA at 4° C. A vibratome (Leica) was used to cut coronal sections at 40 μm and stored in 0.1M PB at 4° C. Fifty-micron sections of 4% paraformaldehyde-fixed human hippocampus were cut on a freezing microtome. Sections were rinsed three times in PBS (each time for 12 minutes) after taken out from the storage protection solution. Both mouse and human brain sections were pretreated with blocking solution (0.3% Triton-X and 10% normal serum in 0.1 M PBS) for 2 hours, and then incubated for 48 hours with the following primary antibodies (in blocking solution at 4° C.): polyclonal anti-Glial Fibrillary Acidic Protein (GFAP, chicken, 1:1000, Millipore, AB5541); polyclonal anti-GABA (guinea pig, 1:1000, Millipore, AB175); polyclonal anti-glutamate (rabbit, 1:300, Abcam, ab9440); polyclonal anti-Glutamate decarboxylase 67 (GAD67, rabbit, 1:100, AnaSpec, 53501); polyclonal anti-GABA transporter 3 (rabbit, 1:100, Abcam, ab431); monoclonal anti-GAD65 (Mouse, 1:200, Developmental Studies Hybridoma Bank); polyclonal anti-GABA$_A$ receptor α5 subunit (rabbit, 1:200, Abcam, ab10098); and monoclonal anti-beta amyloid 1-42 (rabbit, 1:2000, Invitrogen, 700254).

After washing three times in PBS, brain sections were incubated with appropriate secondary antibodies conjugated to Alexa Fluor 488, Alexa Fluor 546, or Alexa Fluor 647 (1:300, Molecular Probes), FITC or TRITC (1:500, Jackson ImmunoResearch) for 2 hours at room temperature. To reveal the location of Aβ plaques, brain sections were incubated in PBS containing 2 μg/mL thioflavin-s for 12 minutes, followed by washing in PBS for three times (3×12 minutes). To reduce lipofucsin like-autofluorescence in human brain sections, the Autofluorescence Eliminator Reagent (Millipore, 2160) was used, which did not adversely affect other fluorescent labeling in the section. Brain sections were mounted onto a glass slide with an anti-fading mounting solution with or without DAPI (Invitrogen). Fluorescent images were obtained with an Olympus confocal microscope (FV1000) and analyzed by Image J software.

Hippocampal Slice Preparation

Mice were anesthetized with 2.5% Avertin. After decapitation, brains were rapidly dissected out and placed in ice-cold cutting solution containing: 79 mM NaCl, 80 mM sucrose, 26 mM NaHCO$_3$, 10 mM glucose, 2.5 mM KCl, 1.25 mM NaH$_2$PO$_4$, 7 mM MgSO$_4$, and 0.5 mM CaCl$_2$ for tonic current recordings. The cutting solution for field EPSP recordings contained: 230 mM sucrose, 26 mM $NaHCO_3$, 20 mM glucose, 2.5 mM KCl, 1.25 mM $NaH_2PO_4$, 10 mM $MgSO_4$, and 0.5 mM $CaCl_2$. Both solutions were bubbled with 95% $O_2$/5% $CO_2$. Hippocampal slices were cut at 350 μm with a vibratome (VT1200S, Leica, Germany) and transferred to a transitional chamber containing one half of cutting solution and one half of standard artificial cerebrospinal fluid (ACSF). The ACSF was composed of: 125.0 mM NaCl, 2.5 mM KCl, 1.3 mM $MgSO_4$, 26.0 mM $NaHCO_3$, 1.25 mM $NaH_2PO_4$, 2.0 mM $CaCl_2$, and mM 10 glucose (290-300 mOsmol; gassed with 95% $O_2$/5% $CO_2$, pH~7.4). Slices were then incubated in ACSF at 32° C. for 30 minutes to recover. Subsequently, slices were maintained at room temperature for another 30 minutes before recording. Individual slices were then transferred to a submerged recording chamber where they were continuously perfused (2-3 mL/minute) with ACSF saturated by 95% $O_2$/5% $CO_2$ at 32° C.

Electrophysiological Recordings

Whole-cell voltage clamp recordings were performed on dentate gyrus granule cells using a pipette solution containing: 135 mM CsCl, 5 mM Na-phosphocreatine, 10 mM HEPES, 5 mM EGTA, 4 mM MgATP, 5 mM QX-314, and 0.5 mM $Na_2GTP$ (pH 7.3 adjusted with CsOH, 280-290 mOsm/L). Pipette resistance was 2-5 MΩ, and series resistance was typically 20-40 MΩ. To record tonic GABA current, 10 μM CNQX and 50 μM DL-APV were added into the ACSF to block glutamate receptors. In some experiments, 5 μM GABA also was added into the ACSF to reveal larger tonic GABA current and increase the signal-to-noise ratio. The total tonic GABA current was revealed by the change of holding current after local perfusion of 100 μM bicuculline (Sigma) to block all $GABA_A$-Rs. The tonic current mediated by α5-$GABA_A$-Rs was revealed by local application of 100 nM L-655,708 (Tocris), a selective inverse agonist for α5 subunit. The membrane potential was held at −70 mV. Data was acquired using pClamp 9 software (Molecular Devices; sampled at 10 kHz and filtered at 1 kHz), and analyzed with Clampfit 9.0 software (Molecular Devices). Field excitatory postsynaptic potentials (fEPSPs) were recorded with glass electrodes filled with 1 M NaCl and 25 mM HEPES (pH 7.3), and were evoked every 20 seconds with a parallel bipolar tungsten electrode (MicroProbes, USA), which was placed at medial perforant path in the dentate gyrus. Three evoked responses were averaged to obtain a data point. Stimulation strength was set to a level that produced a fEPSP amplitude at about 30% of the maximum response. After stable 20 minutes baseline recording, LTP was induced by high frequency stimulation (HFS, 100 pulses at 100 Hz, three times in 20 second intervals).

Drug Treatments

L-655,708 was dissolved at 1 mg/mL in DMSO, and frozen in storage aliquots. The working solution was diluted 10 times in normal saline solution. In order to constantly block the tonic inhibition mediated by α5-$GABA_A$-Rs for a sustained period, L-655,708 (or vehicle) was injected at 1 mg/kg once every day for one week. The last injection was administrated 30 minutes before behavioral test.

Y-Maze Spontaneous Alternation Task

Spontaneous alternation performance was tested as described elsewhere (Oakley et al., *J. Neurosci.*, 26(40): 10129-10140 (2006)). This learning task does not involve any training, reward, or punishment. It allows the assessment of hippocampus-dependent spatial working memory. Each mouse was placed in the center of a symmetrical Y-maze and was allowed to explore freely through the maze during an 8 minute session. The first two minutes were not included for data analysis because mice were exploring new environment. The total number and the sequence of arm entries in the last 6 minutes were recorded and analyzed. Arm entry was defined as the hind paws of the mice had been completely placed in the arm. Analysis was done blind. The percentage of alternation is the number of triads containing entries into all three arms divided by the maximum possible alternations (the total number of arms entered minus 2)×100.

GABA ELISA Assay

GABA concentrations in the mouse hippocampal homogenate were also quantified using mouse GABA ELISA kit (NB-E20434, Novatein Biosciences, Boston, Mass.), performed according to the manufacturer's instructions. Data analysis was performed blindly. Hippocampal homogenate was prepared similar to that described herein for the brain homogenate puff assay.

Data Analysis

Data were represented as mean±SEM. Student's t-test (paired or unpaired) was used for statistical analysis. For comparison among three groups, one-way ANOVA and Tukey-Kramer or Fisher's PLSD post hoc test was used. Statistical significance was set at P<0.05.

Results

5×FAD mice (APPSwF1Lon, PSEN1*M146L*L286V) were used to identify treatment options for Alzheimer's disease (AD). Substantial amyloid deposits were found together with many reactive astrocytes in the dentate gyrus (DG) compared to CA1 region in the hippocampus of 5×FAD mouse brain (FIG. 1, panels a and b). Interestingly, a remarkable increase of both GABA and glutamate content was observed in the reactive astrocytes in the DG of 5×FAD animals compared to wild type (WT) controls (FIG. 2, panels a-c; quantified in FIG. 2, panel c). These high GABA and glutamate-containing reactive astrocytes were surrounding the Aβ plaques labeled by thioflavin-s in the 5×FAD mice (FIG. 2, panel a, merged image). A significant increase of glutamic acid decarboxylase 67 (GAD67), the major enzyme converting glutamate into GABA, also was observed in the reactive astrocytes in DG of 5×FAD mice (FIG. 2, panel b, quantified in FIG. 2, panel c). In contrast, the astrocytes in WT animals did not express significant level of GAD67 (FIG. 2, panel b). To make sure this was not an artifact of transgenic AD animals, human postmortum hippocampal tissue from AD patients (Emory Brain Bank) was examined. There was a substantial increase of GABA content in the reactive astrocytes of AD patients compared to healthy controls (FIG. 2, panel d; quantified in FIG. 2, panel e). Similarly, GAD67 also was significantly increased in the reactive astrocytes of AD patients (FIG. 3; quantified in FIG. 2, panel e). Therefore, reactive astrocytes in the AD brain have an unusual high GABA content, which may be converted from glutamate.

An alternative source of GABA in AD reactive astrocytes is through direct uptake by GABA transporters. The astrocyte-specific GABA transporter GAT-3 was examined, and a significant increase of GAT-3 was found in the reactive astrocytes of AD mouse brain (FIG. 4, panel a; WT, 15.7±3.6 a.u., n=6; AD, 66±14 a.u., n=6; p<0.006, Student's t-test). Such elevated levels of GAT-3 in reactive astrocytes were further confirmed in human AD hippocampal tissue (FIG. 4, panel b; healthy control, 16.0±1.5 a.u., n=6; AD patients, 44.2±1.7 a.u., n=6; p<0.001).

The high level of GAT-3 can either uptake GABA into astrocytes or transport GABA out of astrocytes. The following was performed to determine if the high level of GAT-3 in AD reactive astrocytes transports the high content of GABA outside astrocytes and increases the ambient GABA concentration in surrounding areas. Patch clamp recordings in mouse hippocampal slices were obtained to record tonic GABA currents mediated by extrasynaptic $GABA_A$-Rs, which have high affinity for GABA and are sensitive to subtle changes of ambient GABA concentration (Brickley and Mody, *Neuron*, 73(1):23-34 (2012)). A much larger tonic GABA current was observed in AD dentate granule cells compared to WT controls (FIG. 4, panel c; quantified in FIG. 4, panel e). More importantly, application of a GAT-3 inhibitor SNAP-5114 (50 μM) blocked the majority of the tonic GABA current in AD dentate granule cells (FIG. 4, panel d; quantified in FIG. 4, panels f-g). Thus, the high GABA content in AD reactive astrocytes may be released through GAT-3 to significantly enhance tonic inhibition in DG granule cells.

The following was performed to investigate which subtype of $GABA_A$-Rs mediate the enhanced tonic GABA current in AD dentate granule cells. The δ subunit-containing $GABA_A$-Rs are known to be expressed in the DG granule cells (Sperk et al., *Neuroscience*, 80(4):987-1000 (1997)). THIP (2 μM; 4,5,6,7-tetrahydroisoxazolo[5,4-c]pyridin-3-ol), a selective agonist for δ-$GABA_A$-Rs at low concentration, was applied to hippocampal slices, and the tonic current was examined in dentate granule cells. Surprisingly, although AD granule cells showed significantly larger tonic GABA currents (FIG. 5, panel a; WT, 74.9±8.1 pA, n=16; AD, 117±9.8 pA, n=17; p<0.003; with 5 μM GABA in bath solution), the THIP-induced tonic currents were not different between WT and AD dentate granule cells (FIG. 5, panel b; WT, 65.2±6.6 pA, n=8; AD, 60.7±10.4 pA, n=8; p>0.7). Besides δ-$GABA_A$-Rs, α5-$GABA_A$-Rs also were reported to partially mediate the tonic current in dentate granule cells (Glykys et al., *J. Neurosci.*, 28(6):1421-1426 (2008)). α5-specific inverse agonist L-655,708 was used to examine the tonic current mediated by the α5-$GABA_A$-Rs. Interestingly, the majority of tonic current in AD dentate granule cells was blocked by L-655,708 (FIG. 5, panel c), suggesting a significant contribution of the α5-$GABA_A$-Rs toward the tonic inhibition in the DG of 5×FAD mice. Quantitatively, the tonic current blocked by L-655,708 in AD dentate granule cells was more than doubled that in WT animals (FIG. 5, panel e; WT, 35.4±6.3 pA, n=12; AD, 98.7±12.9 pA, n=9; p<0.001). Since α5-$GABA_A$-Rs are known to be expressed in CA1 pyramidal neurons, the tonic current in CA1 region also was recorded, and tonic currents between WT and AD animals were found to be similar (FIG. 5, panels d and e; WT, 31.2±4.7 pA, n=11; AD, 36.1±6.7 pA, n=9; p>0.5). The proportion of tonic current blocked by L-655,708 also was similar in CA1 neurons (FIG. 5, panel f). These results suggest that the α5-$GABA_A$-Rs were selectively up-regulated in the DG, but not CA1 region, of the 5×FAD animals. To corroborate with the electrophysiology data, immunostaining was performed using α5-specific antibodies. α5-immunopositive signals were clearly detected in the dentate granule layer of WT animals (FIG. 5, panel g) (Hutcheon et al., *Eur. J. Neurosci.*, 19(9):2475-2487 (2004)). Interestingly, the α5 puncta number was significantly increased in AD dentate granule cells (FIG. 5, panel h), consistent with the enhanced tonic current mediated by α5-$GABA_A$-Rs. The majority of α5 puncta were not colocalized with presynaptic GAD65 puncta (FIG. 5, panels g and h, inset), suggesting their extrasynaptic localization. While the α5 puncta number significantly increased in the DG of 5×FAD animals, the GAD65 puncta number did not change in the hippocampus (FIG. 5, panel i and j). Therefore, the α5-$GABA_A$-Rs were up-regulated in AD dentate granule cells and enhanced the tonic inhibition in DG by responding to the increased GABA release from AD reactive astrocytes.

To investigate the functional consequence of enhanced tonic inhibition in the AD brain, the long-term potentiation (LTP) in DG was investigated by performing hippocampal slice recordings. WT animals (6-8 months old) exhibited significant LTP after high frequency stimulation (100 Hz for 1 second, repeat three times with 20 second interval), but the same age 5×FAD animals showed significantly decreased LTP in DG (FIG. 6, panel a; quantified in FIG. 6, panel b). Interestingly, suppression of tonic inhibition, either with SNAP-5114 (50 μM) to block astrocytic GABA release or with L-655,708 (100 nM) to block α5-$GABA_A$-Rs, rescued the LTP impairment in the 5×FAD dentate granule cells (FIG. 6, panels a and b). LTP in the DG of WT animals was not affected by the drug treatment (FIG. 6, panel b). Therefore, the enhanced tonic inhibition triggered by astrocytic GABA release may play a role in the suppression of LTP in the DG of 5×FAD mice.

Figure 6A:
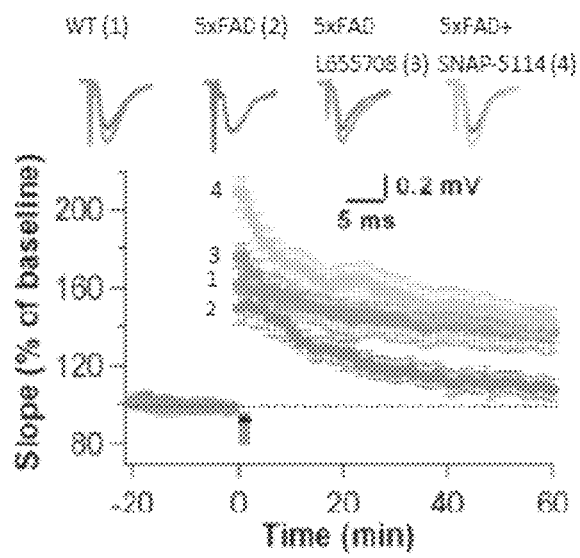
FIGS. 6A-6D contain data demonstrating that blockade of tonic inhibition rescued deficits in LTP and working memory in 5×FAD mice.
Figure 6B:
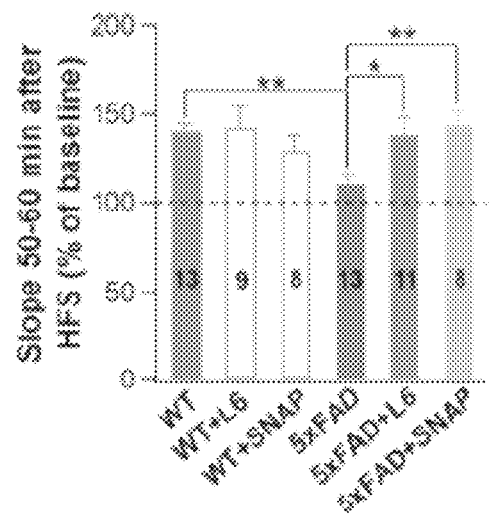
Figure 6C:
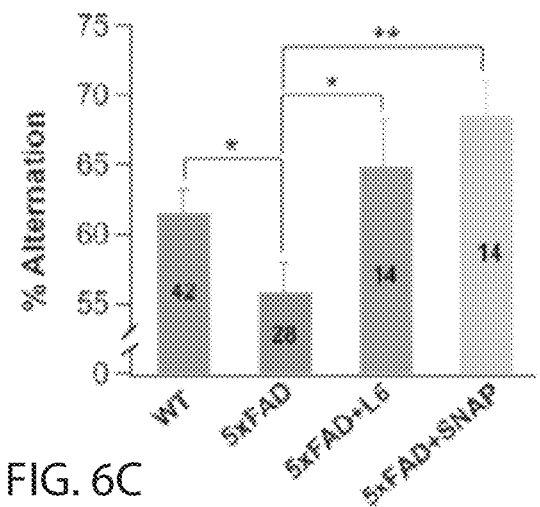
Figure 6D:
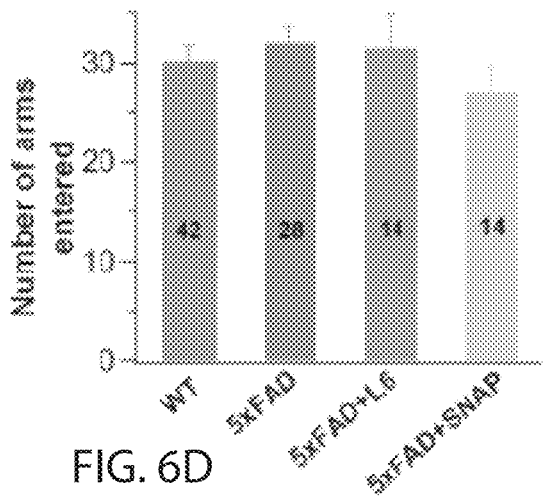

A behavioral analysis was conducted to test the effect of enhanced tonic inhibition on the cognitive function of 5×FAD animals. 5×FAD mice exhibit a significant deficit in the spontaneous alternation test in Y-maze ((Oakley et al., *J. Neurosci.*, 26(40):10129-10140 (2006)). The 5×FAD mice used in this study also exhibited significant memory deficit when placed in a Y-maze to test their sequential entries in each arm of a Y-maze (FIG. 6, panel c). Interestingly, intraperitoneal administration of SNAP-5114 (50 μmol kg-1, i.p., once per day for one week) or L-655,708 (1 mg kg-1, i.p., once per day for one week) rescued the memory deficit in 5×FAD animals (FIG. 6c, p<0.05). The total number of arm entry did not differ among WT, 5×FAD, and 5×FAD plus drug treatment groups (FIG. 6d). Therefore, it was concluded that the abnormal tonic inhibition in DG is an important contributing factor toward the learning and memory deficit in AD.

These results demonstrate that tonic GABA inhibition was abnormally enhanced in the DG of 5×FAD animals, partly due to excessive GABA release from reactive astrocytes and partly due to up-regulated α5-$GABA_A$-Rs in AD dentate granule cells. These results also demonstrated up-regulated α5-$GABA_A$-Rs in the DG of 5×FAD animals and that blocking α5-$GABA_A$-Rs restored the memory deficit.

Further, the results provided herein demonstrate that reactive astrocytes in AD brain have high content of glutamate and GABA as well as GAD67, suggesting that astrocytic glutamate may be converted into GABA under pathological conditions to enhance GABA inhibition and offset glutamate excitotoxicity. However, under chronic excitotoxic and inflammatory stimulation, the excessive GABA release from reactive astrocytes and the up-regulation of the α5-$GABA_A$-Rs may eventually impair LTP and cognitive functions of the AD brain. While GAT-3 was found to be significantly increased in the AD reactive astrocytes, neuronal GABA transporter appeared to be not altered in 5×FAD animals (FIG. 7). These results demonstrate that reducing astrocytic GABA release by inhibiting GAT-3 transporter in reactive astrocytes can be an effective treatment for AD.

A working model regarding memory can be as follows (FIG. 8, panels a and b). In the DG of AD brain, the excitotoxic and inflammatory stimulation can stimulate astrocytes to accumulate high level of glutamate, perhaps through constitutive endocytosis (Jiang and Chen, *J. Neurosci.*, 29(25):8063-8074 (2009)). The glutamate can be converted into GABA and transported out of astrocytes through GAT-3. In the meanwhile, the α5-$GABA_A$-Rs in AD dentate granule cells can be up-regulated to mediate the enhanced tonic inhibition. The abnormally high level of tonic inhibition in the DG of AD brain can suppress LTP and result in the deficits of learning and memory. According to the results provided herein and this working model, the astrocyte-specific GABA transporter GAT-3, the α5-GABA$_A$ receptors, or both can be targeted as treatment options for AD.

Example 2—Brain Homogenate Puff Assay

Brain Homogenate Puff Assay

Three pairs of 6-8 months old WT and AD littermates were sacrificed with 2.5% Avertin, and the brains were quickly removed and put into iced cold PBS to wash out the residual blood. Hippocampi were then dissected out on a cold platform, the wet weight of each sample was recorded, and the samples were placed into autoclaved EP tubes and flash-frozen in liquid nitrogen immediately. The samples were stored in a −80 degree freezer. To make hippocampal homogenate, two freeze-thaw cycles were performed to break the cell membrane before adding 20 μL bath solution per mg tissue into the EP tube. To further fracture the cell, the hippocampal tissue in the EB tube was sonicated for 1 minute on ice. The homogenate was centrifuged for 5 minutes at 5000 g. The supernatant was then aliquoted and stored at −20 degree freezer. To test GABA responses evoked by brain homogenate, HEK293T cells were transfected with α2β3γ2 plasmids, and electrophysiology was performed 24-48 hours after transfection. A bundle of 3-barrel glass pipette was pulled by a P-97 pipette puller. Before electrophysiological recordings, the stored hippocampal homogenate was further diluted by 100 times in bath solution and then used for puffing experiments.

Figure 10R:
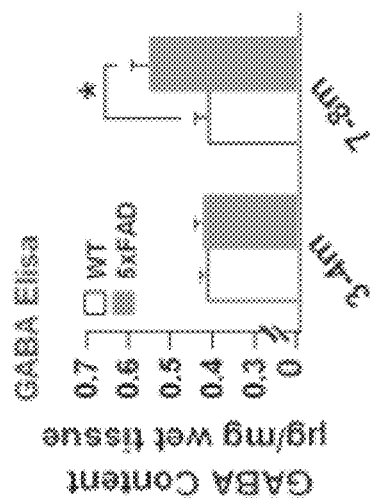
FIGS. 10A-10R. Brain homogenate assay detected higher GABA content in the hippocampal tissue of 5×FAD animals. (a) Schematic diagram illustrating the experimental arrangement of brain homogenate puff (BHP) assay. (b-c) Triple micropipettes filled with the same concentration of GABA (10 µM) evoked the same size of response in a set of HEK cells expressing different level of GABA$_A$-Rs. (d-f) Triple micropipettes filled with different concentrations of GABA (1, 3, 10 µM) evoked proportionally different sizes of responses in HEK cells. (g-o) Three sets of experiments showing responses evoked by WT or AD hippocampal homogenate or GABA (10 µM) in HEK cells expressing GABAA-Rs. AD hippocampal homogenate evoked larger GABA responses in the same cell than that from WT littermate. (p-q) Quantitative data showing increased GABA current evoked by AD hippocampal homogenate compared to that from WT littermate. (r) GABA ELISA assay showing that GABA concentration in the hippocampal tissue increased significantly in old 5×FAD mice (7-8 months, n=5 mice for WT; n=4 mice for 5×FAD), but not in young animals (3-4 months, n=6 mice for WT; n=5 mice for 5×FAD). GABA concentration did not change in WT animals. Data are presented as mean±s.e.m. * represents P<0.05;  represents P<0.01; and * represents P<0.001 (Student's t test).
Figure 10Q:
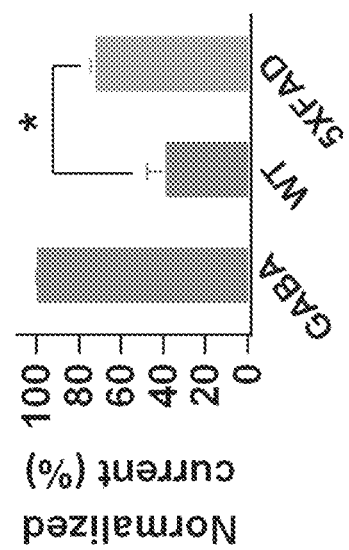
Figure 10P:
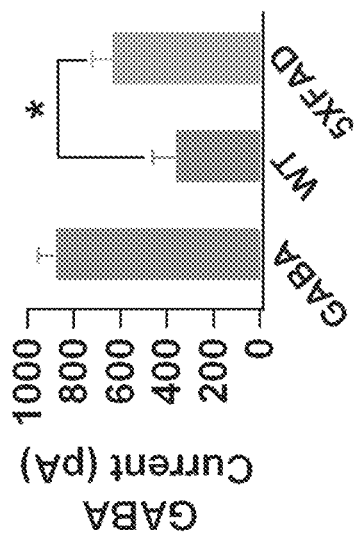

A Brain Homogenate Puff Method for Detecting High GABA Content in AD Hippocampus To independently verify that GABA content is indeed increased in the hippocampus of AD brain, a method to assay GABA concentrations in brain homogenates was developed. HEK293T cells were transfected with GABA$_A$-R α2β3γ2 subunits for detecting GABA responses (Wu et al., *J. Biol. Chem.*, 287(33):27417-27430 (2012); and Wu et al., *J. Biol. Chem.* 288:25053-25065 (2013)). Hippocampal region was dissected out from WT or AD brain and made into homogenate by repeated freeze and thaw and sonication. The hippocampal homogenate was then diluted 100-fold and used to puff onto HEK cells expressing GABA$_A$-Rs (24-48 hours after transfection) to assay GABA responses. This method was named a brain homogenate puff (BHP) assay. To validate this BHP method, a series of control experiments were performed. First, brain homogenate was puffed onto non-transfected HEK cells, and no responses were found (FIG. 9a). Second, bath solution was puffed onto GABA$_A$-R expressing HEK cells, and again no responses were found (FIG. 9b). Third, in order to compare WT and AD brain homogenate side-by-side, a bundle of triple identical micropipettes we made and filled with WT homogenate, GABA (10 μM determined after pilot experiments, in the middle), and AD homogenate (FIG. 10a). When the three micropipettes were filled with the same concentration of GABA, they evoked the same size of GABA responses (FIG. 10b-c). Similarly, when the triple micropipettes were filled with the same brain homogenate, either from WT or AD brain tissue, they also evoked the same size of GABA responses (FIG. 9c-f). Alternatively, when the three micropipettes were filled with different concentrations of GABA (1, 3, and 10 μM), they evoked different sizes of GABA responses (FIG. 10d-f). After these rigorous control experiments, GABA responses were tested in GABA$_A$-R-expressing HEK cells by puffing WT or AD hippocampal homogenate, together with 10 μM GABA (FIG. 10a). In almost every cell tested, the AD hippocampal homogenate consistently evoked larger GABA responses than the WT hippocampal homogenate (FIG. 10g-o). Quantitatively, the GABA current evoked by AD hippocampal homogenate was about twice as large as that evoked by WT hippocampal homogenate (FIG. 10p; WT, 363.7±99.2 pA; AD, 637.1±84.5 pA; n=3 sets, total 24 cells; p<0.03; paired Student's t-test). After normalization, WT hippocampal homogenate-evoked GABA current was 39.1±8.7% and AD hippocampal homogenate-evoked GABA current was 72.7±2.1% of that evoked by 10 μM GABA (FIG. 10q). In addition to electrophysiology assay, a GABA ELISA assay was performed to quantitatively measure the GABA concentration in hippocampal tissue from WT or 5×FAD mice. Interestingly, young animals (3-4 months old) did not exhibit any difference in GABA content (WT, 0.41±0.01 μg mg-1, n=6; 5×FAD, 0.42±0.02 μg mg-1, n=5; p>0.6), but old 5×FAD mice (7-8 months old) exhibited significantly increased GABA content in hippocampal homogenate (FIG. 10r; WT, 0.41±0.03 μg mg-1, n=5; 5×FAD, 0.55±0.04 μg mg-1, n=4; p<0.02). Therefore, the hippocampal tissue in 5×FAD mice has higher GABA content than that in WT mice, likely due to the accumulation of GABA in the reactive astrocytes in 5×FAD brains.

These results demonstrate that a brain homogenate puff assay can be used to determine GABA concentration changes in brain tissue under pathological conditions. Such a brain homogenate puff assay can have the advantage of small variation and high reproducibility. With this brain homogenate puff assay, it was demonstrated that the 5×FAD hippocampal tissue has higher GABA content than the WT hippocampal tissue.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for improving memory of a mammal having Alzheimer's disease, wherein said method comprises administering an inhibitor of GAT-3 polypeptide activity to said mammal, wherein the memory of said mammal improves following said administering.

2. The method of claim 1, wherein said mammal is a human.

3. The method of claim 1, wherein said inhibitor is (S)-SNAP-5114 or NNC 05-2045.

4. The method of claim 1, wherein said memory improves by more than 20 percent.

5. The method of claim 1, wherein said administration comprises an intravenous administration.

6. The method of claim 1, wherein said method comprises administering an inhibitor of $\alpha 5$-$GABA_A$ receptor activity to said mammal.

7. The method of claim 6, wherein said inhibitor of $\alpha 5$-$GABA_A$ receptor activity is L-655,708.

8. The method of claim 1, wherein said inhibitor of $\alpha 5$-$GABA_A$ receptor activity is administered to said mammal after said inhibitor of GAT-3 polypeptide activity is administered to said mammal.

* * * * *

SEQUENCE LISTING

<160> NUMBER OF SEQ ID NOS: 9

<210> SEQ ID NO 1
<211> LENGTH: 19
<212> TYPE: DNA
<213> ORGANISM: Homo sapiens

```
<400> SEQUENCE: 1 gcccttttatt tgaaggcat                                               19

<210> SEQ ID NO 2
<211> LENGTH: 19
<212> TYPE: DNA
<213> ORGANISM: Homo sapiens

<400> SEQUENCE: 2
gcatatggaa gggtactaa                                                19

<210> SEQ ID NO 3
<211> LENGTH: 19
<212> TYPE: DNA
<213> ORGANISM: Homo sapiens

<400> SEQUENCE: 3
gctctttgtg gccatcttt                                                19

<210> SEQ ID NO 4
<211> LENGTH: 19
<212> TYPE: DNA
<213> ORGANISM: Homo sapiens

<400> SEQUENCE: 4
gcacactgcc cgagaaatt                                                19

<210> SEQ ID NO 5
<211> LENGTH: 19
<212> TYPE: DNA
<213> ORGANISM: Homo sapiens

<400> SEQUENCE: 5
gcacaggact tattaacaa                                                19

<210> SEQ ID NO 6
<211> LENGTH: 19
<212> TYPE: DNA
<213> ORGANISM: Homo sapiens

<400> SEQUENCE: 6
ccagtgatag tgggcatat                                                19

<210> SEQ ID NO 7
<211> LENGTH: 19
<212> TYPE: DNA
<213> ORGANISM: Homo sapiens

<400> SEQUENCE: 7
ccacctcacc aagataatt                                                19

<210> SEQ ID NO 8
<211> LENGTH: 19
<212> TYPE: DNA
<213> ORGANISM: Homo sapiens

<400> SEQUENCE: 8
gcctctgatg ttcagtcat                                                19

<210> SEQ ID NO 9
<211> LENGTH: 19
<212> TYPE: DNA
<213> ORGANISM: Homo sapiens
```

-continued

```
<400> SEQUENCE: 9
cctctgatgt tcagtcatt                                              19
```